United States Patent
Orijel et al.

(10) Patent No.: US 10,550,410 B2
(45) Date of Patent: Feb. 4, 2020

(54) ENZYMATIC METHODS FOR ISOBUTANOL PRODUCTION

(71) Applicant: NEWPEK S.A. DE C.V., Nuevo Leon (MX)

(72) Inventors: Claudio Garibay Orijel, Mexico City (MX); Carlos Eduardo Gomez Sanchez, Mexico (MX); Monica Maria Rios Lozano, Mexico City (MX); Jessica Valeria Guerrero Torres, Mexico (MX); Sergio Rossano Becerril, Mexico (MX); Alejandra Cecilia Herrera Ramirez, Mexico (MX); Paola Rocha Ruiz, Mexico (MX); Anne-Laure Patricia Chauvin, Mexico City (MX); Jesus Agustin Badillo Corona, Mexico City (MX); Ivan Alejandro de la Pena Mireles, Nuevo Leon (MX); Jose Raul Ivan Garza Rodriguez, Nuevo Leon (MX)

(73) Assignee: NEWPEK S.A. DE C.V., Nuevo Leon (MX)

(*) Notice: Subject to any disclaimer, the term of this patent is extended or adjusted under 35 U.S.C. 154(b) by 0 days.

(21) Appl. No.: 15/536,417

(22) PCT Filed: Dec. 16, 2014

(86) PCT No.: PCT/IB2014/003204
§ 371 (c)(1),
(2) Date: Jun. 15, 2017

(87) PCT Pub. No.: WO2016/097801
PCT Pub. Date: Jun. 23, 2016

(65) Prior Publication Data
US 2017/0349918 A1    Dec. 7, 2017

(51) Int. Cl.
C12P 7/16    (2006.01)
C12P 7/24    (2006.01)

(52) U.S. Cl.
CPC .. *C12P 7/16* (2013.01); *C12P 7/24* (2013.01)

(58) Field of Classification Search
None
See application file for complete search history.

(56) References Cited

U.S. PATENT DOCUMENTS

| | | |
|---|---|---|
| 2010/0081183 A1 | 4/2010 | Paul et al. |
| 2011/0256595 A1 | 10/2011 | Yoshikuni et al. |
| 2011/0312052 A1 | 12/2011 | Koltermann et al. |
| 2013/0189745 A1 | 7/2013 | Schwarz et al. |
| 2014/0142352 A1 | 5/2014 | Dauner et al. |
| 2014/0186910 A1 | 7/2014 | Maggio-Hall et al. |
| 2014/0193869 A1 | 7/2014 | Blake et al. |
| 2017/0159058 A1 | 6/2017 | Blake et al. |

FOREIGN PATENT DOCUMENTS

| | | |
|---|---|---|
| DE | 40 20 406 A1 | 1/1992 |
| EP | 1 731 618 A1 | 12/2006 |
| EP | 2 204 453 A1 | 7/2010 |
| EP | 2551254 A1 | 1/2013 |
| EP | 2 700 714 A1 | 2/2014 |
| JP | 2000-342294 A | 12/2000 |
| JP | 2012-513759 A | 6/2012 |
| WO | WO 2011/115151 A1 | 9/2011 |
| WO | WO 2013/117251 A1 | 8/2013 |
| WO | WO 2014/028642 A1 | 2/2014 |
| WO | WO 2014/100722 A1 | 6/2014 |

OTHER PUBLICATIONS

Qureshi et al. Process integration for simultaneous saccharification, fermentation, and recovery (SSFR): Production of butanol from corn stover using Clostridium beijerinckii P260, Bioresource Technology (2014, E pub. Dec. 7, 2013), 154: 222-228.*
Extended European Search Report dated Jun. 8, 2018 in corresponding European Patent Application No. 14908338.8, 9 pages.
Sue Retka Schill: "ASTM publishes D7862 standard for butanol", XP055478700, Oct. 3, 2013, 2 pages, Retrieved from the Internet: URL:http://biomassmagazine.com/articles/95 07/astm-publishes-d7862-standard-for-butanol [retrieved on May 28, 2018].
ASTM International: "ASTM 07862-17, Standard Specification for Butanol for Blending with Gasoline for Use as Automotive Spark-Ignition Engine Fuel", XP055478696, May 28, 2018, 8 pages, Retrieved from the Internet: URL:https://www.astm.org/Standards/07862.h tm [retrieved on May 28, 2018].
International Search Report and Written Opinion dated Jul. 23, 2015, in PCT/IB2014/003204 filed Dec. 16, 2014.
Niemisto, Johanna, "Towards Sustainable and Efficient Biofuels Production", Acta, University of Oulu Graduate School, (2014). 115 pages.
Office Action dated May 13, 2019, in Japanese Patent Application No. 2017-533487 (with English translation).

* cited by examiner

*Primary Examiner* — Iqbal H Chowdhury
(74) *Attorney, Agent, or Firm* — Oblon, McClelland, Maier & Neustadt, L.L.P.

(57) ABSTRACT

The present invention relates to a process of producing isobutanol, including: mixing water, lactate, an enzyme mixture including at least one enzyme, at least one cofactor, and at least one coenzyme, to prepare a reaction mixture; allowing catalytic conversions of lactate in the reaction mixture for a sufficient amount of time to produce isobutanol; and separating the isobutanol from a reactant obtained by the catalytic conversions, in which the conversion of lactate into isobutanol is in association with a $NADH^+$/NADH and/or $NADP^+$/NADPH regenerating system.

33 Claims, 4 Drawing Sheets

ENZYMATIC METHODS FOR ISOBUTANOL PRODUCTION

BACKGROUND OF THE INVENTION

Technical Field

The present invention relates to the field of biotechnology. Specifically, the present invention relates to a process for producing isobutanol, in which lactate is catalytically converted into isobutanol.

Background 4-carbon alcohol compounds such as n-butanol and isobutanol are important industrial chemicals, and are useful as fuel additives, as feedstock in the plastic industry, and as agents of food-grade extractions. Each year, greater amounts of those alcohols are produced in the petrochemical industry, due to an increase in the demand.

Typically, these alcohols are produced by chemical synthesis or by biological processes. Both n-butanol and isobutanol can be produced chemically by hydroformylation of propylene, a process in which propylene contacts a catalyst comprising rhodium, leading to the hydroformylation of propylene to form butyraldehyde and isobutyraldehyde. Whereafter, the aldehydes are hydrogenated to form the corresponding alcohol, either butanol or isobutanol, as described in the European patent EP1733003 B1 (the contents of which are hereby incorporated by reference in its entirety). Furthermore, n-butanol can be produced biologically by a well-known metabolic pathway named ABE fermentation (Jones and Woods, 1986; Berezina et al, 2012). This fermentation is widely used in industry, using *Clostridium acetobutylicum*, a widely used microorganism.

In regard to isobutanol, there is no genetically unmodified microorganism that is able to produce sufficient quantities of this compound for an industrial process. Although it is known that *Saccharomyces cerevisiae* is able to produce isobutanol when the nitrogen source is valine (Dickinson et al, 1998), a culture media using this amino acid as a nitrogen source is not economically viable.

Therefore, isobutanol has been conventionally produced by fermentation using genetically modified organisms. Genetically modified organisms such as *Saccharomyces cerevisiae* and *Escherichia coli* have been generally known to increase the production of isobutanol, as described in the U.S. Pat. Nos. 7,851,188, 7,910,342, 7,993,889, 8,017,375, 8,017,376, 8,071,358, 8,097,440, 8,133,715, 8,153,415, 8,158,404, 8,178,328, 8,232,089, 8,241,878, 8,273,558, 8,273,565, and 8,283,144 (the contents of which are hereby incorporated by reference in their entirety). The raw material described in those patents is usually a carbohydrate, such as glucose, sucrose or fructose, as highlighted in the U.S. Pat. Nos. 7,851,188, 8,017,375, 8,178,328, and 8,283,144. Although this technology has evolved, it is important to note that there are various drawbacks associated with the use of genetically modified organisms to produce isobutanol, such as:

1. Large amounts of viable cells must be present to carry out the process efficiently. If there are small amounts of cells, the fermentation process becomes very slow. This fact has been well-known in the art.

2. Introducing an exogenous metabolic pathway into an organism implies an increase in the competition among its own metabolic pathways, as the carbon flow is divided between the microbial growing and isobutanol production. It prevents processes from reaching values close to the theoretical yield (for example, for the case of glucose, 0.411 grams of isobutanol is obtained from one gram of glucose). Therefore, to reach acceptable yields, it is not enough to express the metabolic pathway for the production of isobutanol; it is also required to remove genes from the metabolic pathway to reduce competition for the production of isobutanol. For example, genes encoding the enzyme pyruvate decarboxylase have been removed are described in U.S. Pat. Nos. 7,993,889, 8,017,375, 8,133,715, 8,153,415, 8,178,328, and 8,273,565. Additionally, genes encoding the enzyme glyceraldehyde 3-phosphate dehydrogenase have also been removed, as described in U.S. Pat. Nos. 8,071,358, 8,097,440, 8,133,715, 8,153,415, and 8,273,565. Similarly, genes encoding the enzyme aldehyde dehydrogenase have been removed, as described in the U.S. Pat. No. 8,158,404.

3. Furthermore, to increase the yield of isobutanol, it is also required to overexpress endogenous and/or exogenous genes to establish the biochemical pathway of the isobutanol production. For example, overexpression of the aft gene increases activity of the enzymes involved in the synthesis of isobutanol, as described in the U.S. Pat. Nos. 8,017,376, 8,071,358, and 8,273,565.

4. It has been generally known in the art that removing and/or overexpressing genes, as described in 2 and 3 above, often makes organisms metabolically unstable.

Accordingly, it is desirable to have a process in which no interaction or competition for the various substrates takes place, and no growth of microorganism associated with the process takes place.

In view of such need, European patent EP2204453 describes an enzymatic isobutanol production (the contents of which are hereby incorporated by reference in its entirety). However, to carry out the process, glucose is used as a raw material, which requires at least 5 enzymes to be converted into pyruvate. In addition to using several enzymes to produce pyruvate, patent EP2204453B1 describes that the operating temperature of the system is above 50° C. This is due to the reducing efficiency of enzymes that catalyze the generation of pyruvate from glucose at lower temperatures. On the other hand, some enzymes that catalyze conversion of pyruvate into isobutanol operate efficiently at temperatures of from 20° C. to 37° C. In consequence, some of those enzymes may lose their catalytic activities over a short period of time because of the incompatibility of the enzymatic systems, as mentioned in examples of the patent EP2204453, specifically in Example 10.

On the other hand, the patent application publication EP2700714A1 (the contents of which are hereby incorporated by reference in its entirety) describes a very similar scheme to the patent EP2204453B1, but uses at least 13 enzymes to carry out the process.

In addition to the above-described drawbacks associated with the conventional processes of producing isobutanol, it should be noted that there is no process in the prior art, in which isobutanol is produced from lactate, and in which the production of isobutanol is carried out enzymatically. Moreover, there is no process in the prior art in which the action of those enzymes regenerates the electron acceptor and donor molecules in a continuous and stable manner for long periods of time.

SUMMARY

Therefore, an object of the present invention is to provide an enzymatic method for the production of isobutanol from lactate, wherein the production of isobutanol is associated with the NAD+/NADH and/or NADP+/NADPH regeneration and in which this process may not be associated with growth of a microorganism.

Another object of the present invention is to associate the production of isobutanol from lactate, with a NAD+/NADH regenerating system.

A further object of the present invention is to associate the production of isobutanol from lactate, with a NADP+/NADPH regenerating system.

Meanwhile, another object of the present invention is to associate the production of isobutanol from lactate, with a regenerating system of a mixture of NAD+/NADH and NADP+/NADPH.

Similarly, an object of the present invention is to provide a method in which the production of isobutanol from lactate is associated with a NAD+/NADH and/or NADP+/NADPH regenerating system, and which can be performed in a controlled environment, in which either of the components of the reaction mixture can be recirculated to the process.

Another object of the present invention is to develop a method in which the NAD+/NADH and/or NADP+/NADPH regenerating system is associated with isobutanol production from lactate in a batch process.

Another object of the present invention is to develop a method in which the NAD+/NADH and/or NADP+/NADPH regenerating system is associated with isobutanol production from lactate in a semi-continuous process.

Another object of the present invention is to develop a method in which the NAD+/NADH and/or NADP+/NADPH regenerating system is associated with isobutanol production from lactate in a continuous process.

These and other objects, alone or in combinations thereof, have been satisfied by the discovery of a process of producing isobutanol, including: mixing water, lactate, an enzyme mixture including at least one enzyme, at least one cofactor, and at least one coenzyme, to prepare a reaction mixture; allowing catalytic conversions of lactate in the reaction mixture for a sufficient amount of time to produce isobutanol; and separating the isobutanol from a reactant obtained by the catalytic conversions in B). The conversion of lactate into isobutanol in B) is in association with a NAD+/NADH and/or NADP+/NADPH regenerating system.

DETAILED DESCRIPTION

Figure 1:
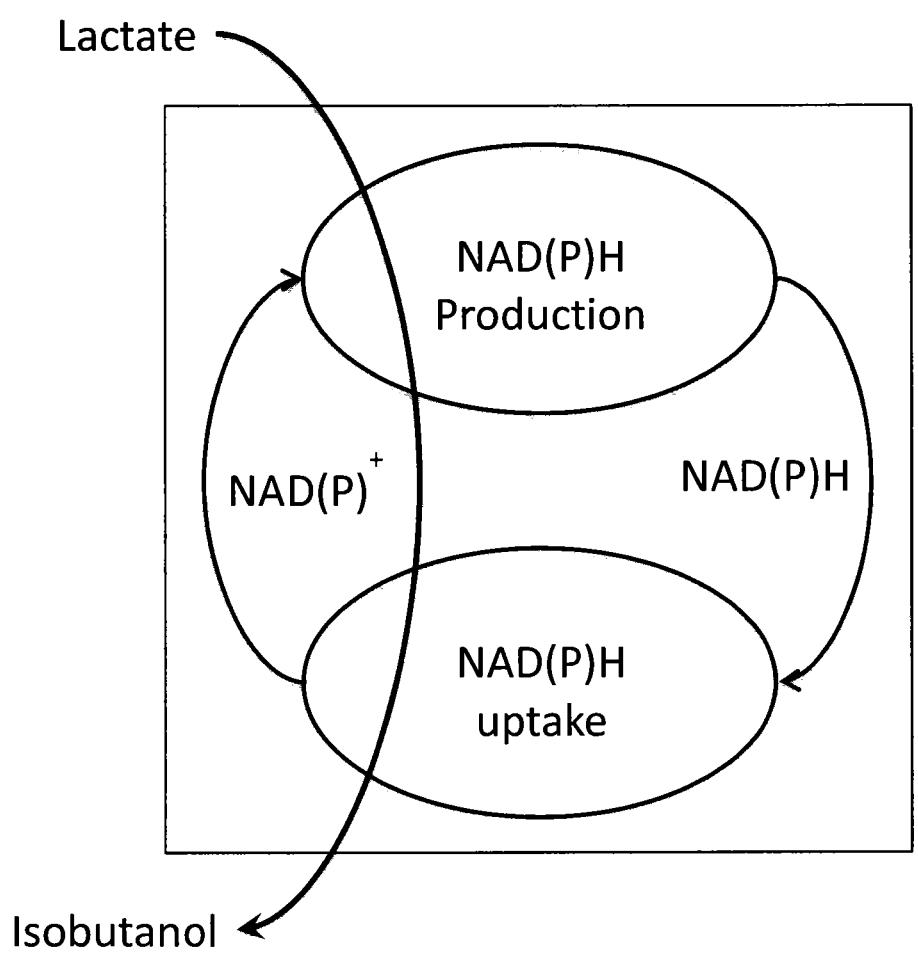
FIG. 1 shows a scheme of the NAD+/NADH and/or NADP+/NADPH regenerating system associated with isobutanol production from lactate.

In order to understand the objects of the present invention, the following definitions and abbreviations are provided:

The terms "lactic acid", "lactate", "2-hydroxypropanoic acid" and "α-hydroxypropanoic acid" refer to the same molecule, wherein such molecule has three carbons and has the following molecular formula: $H_3C-CHOH-COOH$ ($C_3H_6O_3$). For the purposes of this invention, the term "lactic acid" refers to any isomer or mixture of isomers reported in the international databases with the identification numbers CAS 50-21-5, 79-33-4, 10326-41-7, 598-82-3, which may be L-lactate or D-lactate or a mixture of both in any proportion. Also, for the purposes of this invention, the term "lactate" is equivalent to "lactic acid", since in solution and depending on the pH, "lactic acid" may be present in its ionic form. "Lactate" can be obtained in different ways, whether biological or chemical. In a biological way, the "lactate" can be obtained, for example, by the fermentation of organic compounds. Some of the "lactate"-producing organisms include *Escherichia coli, Lactobacillus casei, Lactobacillus delbrueckii, Lactococcus lactis*, etc. Chemically, the "lactate" can be obtained from ethanol, sodium cyanide and sulfuric acid; the process terminates with a nucleophilic attack of the cyanide to the carbonyl group of the aldehyde to form the nitrile of the lactic acid in a racemic form. The nitrile is hydrolyzed in the presence of water and an excess of sulfuric acid to yield the free "lactic acid".

The terms "pyruvate", "pyruvic acid", "2-oxopropanoic acid," "α-ketopropionic acid", "pyroracemic acid" and "acetylformic acid" refer to the same molecule; such molecule has three carbons and has the following molecular formula $CH_3COCOOH$ ($C_3H_4O_3$, CAS: 127-17-3).

The terms "2-acetolactic acid," "2-acetolactate," "2-hydroxy-2-methyl-3-oxobutanoic acid" and "2-acetyl lactic acid" refer to the same molecule; such molecule has five carbons and has the following molecular formula $CH_3COC(CH_3)OHCOOH$ ($C_5H_8O_4$, CAS: not available).

The terms "2,3-dihydroxyvalerate", "2,3-dihydroxy-3-methylbutanoate", "2,3-dihydroxy-isovalerate", "2,3-dihydroxy-isovaleric acid" refer to the same molecule; such molecule has five carbons and has the following molecular formula $(CH_3)_2COHCHOHCOOH$ ($C_5H_{10}O_4$, CAS: 1756-18-9).

The terms "ketoisovaleric acid", "ketoisovalerate", "3-methyl-2-oxobutanoic acid", "2-oxoisovalerate", "2-oxoisopentanoate" and "2-ketovaline" refer to the same molecule; such molecule has five carbons and has the following molecular formula $(CH_3)_2CHCOCOOH$ ($C_5H_8O_3$, CAS: 759-05-7).

The terms "isobutyraldehyde", "2-methylpropanal" and "2-methylpropionaldehyde" refer to the same molecule; such molecule has four carbons and the following molecular formula $(CH_3)_2CHCHO$ ($C_4H_8O$, CAS: 78-84-2).

The terms "isobutanol", "isobutyl alcohol" and "2-methyl-1-propanol" refer to the same molecule; such molecule has four carbons and has the following molecular formula $(CH_3)_2CHCH_2OH$ ($C_4H_{10}O$, CAS: 78-83-1).

The terms "reduced nicotinamide adenine dinucleotide (NADH)" and "nicotinamide adenine dinucleotide (NAD+)" refer to molecules of the cellular metabolism that transport electrons from one molecule to other, and carry out oxidation-reduction reactions, or redox reactions.

The terms "reduced nicotinamide adenine dinucleotide phosphate (NADPH)" and "nicotinamide adenine dinucleotide phosphate (NADP+)" refer to molecules of the cellular metabolism that transport electrons from one molecule to other, and carry out oxidation-reduction reactions, or redox reactions.

For the purpose of this invention, the term "NAD(P)+" is equivalent to the term "NAD+" and/or "NADP+", and the use of the term "NAD(P)H" is equivalent to the terms "NADH" and/or "NADPH".

The term "theoretical yield" refers to the maximum amount of product that can be obtained by a reaction, and it is calculated by a stoichiometric equation. The theoretical yield may be compared with a theoretical amount of product obtained by experimental reactions calculated based on the stoichiometry of the reaction.

The term "experimental yield" refers to the amount of product that is obtained experimentally by a chemical reaction with respect to the amount of consumed substrates.

The term "conversion efficiency" refers to the percentage obtained from the ratio between the experimental and the theoretical yields, and its value may vary from 0 to 100%.

The terms "redox reaction" and "redox reactions" refer to a biochemical reaction that is mediated by the action of an enzyme, wherein a compound is reduced and another is oxidized. These reactions may occur in the cells due to the presence of NADH or NADPH (oxidizing agents) and $NAD^+$ or $NADP^+$ (reducing agents).

The terms "polypeptide" and "enzyme" refer to an organic molecule including amino acid residues that is able to perform conversion reactions from a starting compound to a final compound, wherein the starting and the final compounds may be molecularly and/or spatially different.

The terms "gene" or "genes" refer to biological molecules, which are composed of nitrogen compounds or bases known in the prior art as adenine, guanine, cytosine and thymine. The genes are molecules that transmit information in a cell for the synthesis of biological enzymes.

The term "reactor" refers to a physical container built from a suitable material, in which, in a controlled manner, a chemical, biochemical, biological reaction or combinations thereof can occur. Different types of reactors can be found in the prior art. As an example, continuous stirred-tank reactor (CSTR), plug flow reactor, fluidized bed reactor, and packed bed reactor (PBR) are mentioned. Some characteristics of the reactors may include: a) its corrosion resistance due to the reactions; b) its ability to monitor and control operating variables such as temperature, stirring, pH, concentration of dissolved gases, pressure, etc; c) its operating mode, which can be in continuous, semi-continuous or batch (various operating modes in which a reactor can operate may be known in the art); d) its ability to use different types of catalysts to carry out the reaction; for example, the catalysts may be dissolved or may be trapped or immobilized (various modes in which a catalyst can be catalyzing the reaction may be known in the art).

The term "cofactors" refers to inorganic compounds, which are required for the action of enzymes, eg. $Mg^{2+}$, $Fe^{2+}$, $Zn^{2+}$, $Na^+$, $K^+$, $Co^{2+}$, $Ni^{2+}$, $Mn^{2+}$, etc.

The term "substrate" refers to a molecule on which an enzyme reacts. The enzyme may be specific and selective for a substrate.

The terms "enzyme mixture" and "mixture of enzymes" refer to a set of enzymes found in the same solution, which enables the production of isobutanol from lactate. The enzyme mixture and mixture of enzymes may be prepared prior to be mixed with lactate or other components employed in the process of the present invention. In one aspect, the enzymes may be mixed in a container such as a pipe, a tank, or a reactor, prior to be mixed with lactate or the other components.

The concentration of enzyme(s) in the enzyme mixture may be greater than 0.001 g/L, greater than 0.01 g/L, or preferably greater than 0.1 g/L.

When the enzyme(s) is/are immobilized as defined below, the concentration of enzyme(s) in the enzyme mixture may be greater than 0.001 g/g, greater than 0.01 g/g, or preferably greater than 0.1 g/g, of the carrier.

In one aspect of the present invention, the enzyme mixture may include at least one of lactate dehydrogenase (EC 1.1.1.27 and/or EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.1 y/o EC 1.1.1.2), and analogues thereof. In one preferred aspect of the present invention, the enzyme mixture may include lactate dehydrogenase (EC 1.1.1.27 and/or EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), and alcohol dehydrogenase (EC 1.1.1.1 y/o EC 1.1.1.2).

The term "coenzyme" refers to organic and non-protein compounds that are essential for the activity of some enzymes. Examples of coenzyme include "flavin adenine dinucleotide (FAD)", "thiamine pyrophosphate (ThPP)", "flavin mononucleotide (FMN)", etc.

The term "reaction mixture" refers to the group of chemical compounds in aqueous, oil, gaseous, or solid phases, which may be subject to catalytic reactions by a polypeptide or mixture of polypeptides. A reaction mixture may include, or may be composed of, an enzyme mixture, cofactors, coenzymes, $NAD^+$/NADH and/or $NADP^+$/NADPH, and lactate. The reaction mixture may be prepared by mixing the chemical compounds in a container that is appropriate to prepare the mixture. For example, a pipe, a tank, or a reactor may be utilized to prepare the reaction mixture. A reaction mixture may be prepared by mixing the chemical compounds by an appropriate method to promote interactions between the enzyme(s) and the substrate(s).

When the reaction mixture includes lactate, the concentration of lactate in the reaction mixture may be at least 1 g/L, 20 g/L, 100 g/L, 200 g/L, or preferably 300 g/L.

The term "sequential" refers to the orderly transformation of lactate to pyruvate by the enzyme lactate dehydrogenase (EC 1.1.1.27 and/or EC 1.1.1.28), pyruvate into 2-acetolactate by the enzyme acetolactate synthase (EC 2.2.1.6), 2-acetolactate into 2,3-dihydroxyvalerate by the ketol acid reductoisomerase (EC 1.1.1.86), 2,3-dihydroxyisovalerate into ketoisovalerate by the enzyme dihydroxy acid dehydratase (EC 4.2.1.9), ketoisovalerate into isobutyraldehyde by the enzyme ketoacid decarboxylase (EC 4.1.1.72) and isobutyraldehyde into isobutanol by the enzyme alcohol dehydrogenase (EC 1.1.1.1 and/or EC 1.1.1.2).

The term "multi-enzyme system" refers to a set of enzymes that sequentially convert lactate into isobutanol.

The term "gene deletion" refers to a process of deleting a DNA region encoding a protein.

The term "exogenous gene" refers to a DNA region encoding a protein foreign to the organism.

The term "endogenous gene" refers to a DNA region encoding a native protein in the organism.

The term "overexpression" refers to increased expression levels of a protein encoded by an endogenous- or an exogenous-gene.

The term "regeneration of $NAD^+$/NADH and/or $NADP^+$/NADPH" refers to: the conversion of $NAD^+$ and/or $NADP^+$ molecules to NADH and/or NADPH molecules resulting from the action of any enzyme that may catalyze these conversions; and the conversion of NADH and/or NADPH molecules into $NAD^+$ and/or $NADP^+$ resulting from the action of any enzyme that may catalyze these conversions. Those conversions can be found in the same reaction system.

The term "free enzyme" refers to an enzyme distributed in a solution.

The term "free enzymes" refers to a set of enzymes distributed in a solution.

The term "carrier" refers to a solid or semi-solid inert matrix, which preferably does not change its protein structure. The carrier may be any kinds of carriers that may be suitable to immobilize an enzyme. Examples of the carrier may include, but are not limited to, zeolite, activated carbon, acrylamide, silica gel, agarose, alginate, sand, or any combinations thereof.

The term "immobilized enzyme" refers to an attached, trapped, embedded, adhered, adsorbed, bound, secured, etc., enzyme by any physical or chemical method in/on a "carrier".

The term "immobilized enzymes" refers to a set of attached trapped, embedded, adhered, adsorbed, bound, secured, etc., enzymes, by any physical or chemical method in/on a "carrier".

The terms "L-lactate dehydrogenase", "L(+)-nLDH", "L-(+)-lactate dehydrogenase", "L-lactic dehydrogenase", "L-lactic acid dehydrogenase", "L-lactate dehydrogenase NAD$^+$-dependent" and "L-lactic dehydrogenase" (EC 1.1.1.27) refer to a polypeptide having catalytic activity, wherein the catalytic activity includes converting the compound L-lactate into pyruvate. However, there may exist other enzymes that are not classified in this group of enzymes that catalyze the conversion reaction of L-lactate into pyruvate. Such enzymes will be considered as analogues of L-lactate dehydrogenase. Examples of the enzymes that can catalyze the conversion reaction of L-lactate into pyruvate are described in Table 1. The enzymes described in Table 1 are shown for reference only, since there are many databases where more examples of these enzymes can be found, such as GeneBank (http(colon)//www(dot)ncbi(dot)nlm(dot)nih(dot)gov), Kyoto Encyclopedia of Genes and Genomes (http(colon)//www(dot)keg(dot)jp), Braunschweig Enzyme Database (http(colon)//www(dot)brenda-enzymes(dot)org), etc.

TABLE 1

Examples of the L-lactate dehydrogenases, which can be used to convert L-lactate into pyruvate.

| Gene Name | Microorganism |
| --- | --- |
| L-Lactate dehydrogenase APECO1_2404 | *Escherichia coli* APEC O1 |
| L-Lactate dehydrogenase ECS88_4540 | *Escherichia coli* O45:K1:H7 S88 |
| L-Lactate dehydrogenase ECOK1_4554 | *Escherichia coli* IHE3034 |
| L-Lactate dehydrogenase ldhal6b | *Mus musculus* |
| L-Lactate dehydrogenase ldha | *Cricetulus griseus* |
| L-Lactate dehydrogenase ldhb | *Pongo abelii* |
| L-Lactate dehydrogenase LDHAL6B | *Canis familiaris* |
| L-Lactate dehydrogenase ldh1 | *Staphylococcus aureus* subsp. *aureus* COL (MRSA) |
| L-Lactate dehydrogenase ldh | *Corynebacterium glutamicum* K051 |
| L-Lactate dehydrogenase ldh | *Sorangium cellulosum* So ce 56 |
| L-Lactate dehydrogenase lhd | *Bacillus subtilis* subsp. *subtilis* 168 |
| L-Lactate dehydrogenase ldh | *Lactococcus lactis* subsp. *lactis* Il1403 |
| L-Lactate dehydrogenase AFUA_5G14800 | *Aspergillus fumigatus* |
| L-Lactate dehydrogenase Ent638_2002 | *Enterobacter* sp. 638 |
| L-Lactate dehydrogenase SPAP_1246 | *Streptococcus pneumoniae* AP200 |

The terms "D-lactate dehydrogenase", "D-specific lactic dehydrogenase", "D-(−)-lactate dehydrogenase (NAD$^+$)", "D-lactic acid dehydrogenase", "D-lactic dehydrogenase" (EC 1.1.1.28) refer to a polypeptide having catalytic activity, wherein the catalytic activity includes converting the compound D-lactate into pyruvate. However, there may exist other enzymes that are not classified in this group of enzymes that catalyze the conversion reaction of D-lactate into pyruvate. Such enzymes will be considered as analogues of D-lactate dehydrogenase. Examples of the enzymes that can catalyze the conversion reaction of D-lactate into pyruvate are described in Table 2. The enzymes described in Table 2 are shown for reference only, since there are many databases where more examples of these enzymes can be found, such as GeneBank, Kyoto Encyclopedia of Genes and Genomes, Braunschweig Enzyme Database, etc.

TABLE 2

Example of the D-lactate dehydrogenases, which can be used to convert D-lactate into pyruvate.

| Gene Name | Microorganism |
| --- | --- |
| D-Lactate dehydrogenase ldhA | *Escherichia coli* K-12 MG1655 |
| D-Lactate dehydrogenase ldhA | *Escherichia coli* O26:H11 11368 (EHEC) |
| D-Lactate dehydrogenase ldhA | *Escherichia coli* PMV-1 |
| D-Lactate dehydrogenase ldhA | *Escherichia coli* O145:H28 RM13514 (EHEC) |
| D-Lactate dehydrogenase dld | *Shigella boydii* Sb227 |
| D-Lactate dehydrogenase Spea_0742 | *Shewanella pealeana* |
| D-Lactate dehydrogenase ldhA | *Treponema pallidum* Fribourg-Blanc |
| D-Lactate dehydrogenase M062_04545 | *Pseudomonas aeruginosa* RP73 |
| D-Lactate dehydrogenase ldld | *Acinetobacter* sp. ADP1 |
| D-Lactate dehydrogenase PC1_2294 | *Pectobacterium carotovorum* subsp. *carotovorum* PC1 |
| D-Lactate dehydrogenase ldld | *Neisseria meningitidis* WUE 2594 (serogroup A) |
| D-Lactate dehydrogenase ldhA | *Cytophaga hutchinsonii* |
| D-Lactate dehydrogenase plabr_4649 | *Planctomyces brasiliensis* |
| D-Lactate dehydrogenase sthe_3421 | *Sphaerobacter thermophilus* |
| D-Lactate dehydrogenase alfi_3240 | *Alistipes finegoldii* |

The terms "acetolactate synthase", "acetolactate synthase", "alpha-acetohydroxy acid synthetase", "alpha-acetohydroxyacid synthase", "alpha-acetolactate synthase", "alpha-acetolactate synthetase", "acetohydroxy acid synthetase", "acetohydroxyacid synthase", "acetolactate pyruvate-lyase (carboxylating)", "acetolactic synthetase" (EC 2.2.1.6) refer to a polypeptide having catalytic activity, wherein the catalytic activity includes converting the compound pyruvate into 2-acetolactate. However, there may exist other enzymes that are not classified in this group of enzymes that catalyze the conversion reaction of pyruvate into 2-acetolactate. Such enzymes will be considered as analogues of acetolactate synthase. Examples of the enzymes that can catalyze the conversion reaction of pyruvate into 2-acetolactate are described in Table 3. The enzymes described in Table 3 are shown for reference only, since there are many databases where more examples of these enzymes can be found, such as GeneBank, Kyoto Encyclopedia of Genes and Genomes, Braunschweig Enzyme Database, etc.

TABLE 3

Examples of the acetolactate synthases, which can be used to convert pyruvate into 2-acetolactate.

| Gene Name | Microorganism |
| --- | --- |
| Acetolactate synthase ilvH | *Escherichia coli* str. K-12 substr. MG1655 |

TABLE 3-continued

Examples of the acetolactate synthases, which can be used to convert pyruvate into 2-acetolactate.

| Gene Name | Microorganism |
| --- | --- |
| Acetolactate synthase ilvB | *Escherichia coli* str. K-12 substr. MG1655 |
| Acetolactate synthase ilvN | *Escherichia coli* str. K-12 substr. MG1655 |
| Acetolactate synthase ilvI | *Escherichia coli* str. K-12 substr. MG1655 |
| Acetolactate synthase ilvH | *Escherichia coli* str. K-12 substr. W3110 |
| Acetolactate synthase ilvM | *Escherichia coli* str. K-12 substr. MG1655 |
| Acetolactate synthase ilvB I | *Escherichia coli* str. K-12 substr. W3110 |
| Acetolactate synthase ilvN I | *Escherichia coli* str. K-12 substr. W3110 |
| Acetolactate synthase ilvI III | *Escherichia coli* str. K-12 substr. W3110 |
| Acetolactate synthase ilvB I, | *Mycobacterium tuberculosis* H37Rv |
| Acetolactate synthase ilvB | *Bacillus subtilis* subsp. *subtilis* str. 168 |
| Acetolactate synthase iLV2 | *Saccharomyces cerevisiae* S288c chromosome XIII |
| Acetolactate sintasa iLV6 | *Saccharomyces cerevisiae* S288c chromosome III |
| Acetolactate synthase ilvH 3 | *Methanococcus aeolicus* Nankai-3 |
| Acetolactate synthase CSR1 | *Arabidopsis thaliana* chromosome 3 |

The terms "keto acid reductoisomerase", "ketol acid reductoisomerase", "dihydroxyisovalerate dehydrogenase (isomerizing)", "acetohydroxy acid isomeroreductase", "alpha-keto-beta-hydroxylacyl reductoisomerase" "2-hydroxy-3-keto acid reductoisomerase", "acetohydroxy acid reductoisomerase", "acetolactate reductoisomerase" and "dihydroxyisovalerate (isomerizing) dehydrogenase" (EC 1.1.1.86) refer to a polypeptide having catalytic activity, wherein the catalytic activity includes converting the 2-acetolactate into 2,3-dihydroxyvalerate. However, there may exist other enzymes that are not classified in this group of enzymes that catalyze the conversion reaction of 2-acetolactate into 2,3-dihydroxyvalerate. Such enzymes will be considered as analogues of keto acid reductoisomerase. Examples of the enzymes that can catalyze the conversion reaction of 2-acetolactate into 2,3-dihydroxyvalerate are described in Table 4. The enzymes described in Table 4 are shown for reference only, since there are many databases where more examples of these enzymes can be found, such as GenBank, Kyoto Encyclopedia of Genes and Genomes, Braunschweig Enzyme Database, etc.

TABLE 4

Examples of the keto acid reductoisomerases, which can be used to convert 2-acetolactate into 2,3-dihydroxyvalerate.

| Gene Name | Microrganismo |
| --- | --- |
| Keto acid reductoisomerase ilvC | *Escherichia coli* str. K-12 substr. MG1655 |
| Keto acid reductoisomerase ilvC | *Escherichia coli* str. K-12 substr. W3110 |
| Keto acid reductoisomerase ilvC | *Corynebacterium glutamicum* ATCC 13032 |
| Keto acid reductoisomerase ilvC | *Corynebacterium glutamicum* K051 |
| Keto acid reductoisomerase ilvC | *Salmonella enterica* subsp. *serovar Typhimurium* str. LT2 |
| Keto acid reductoisomerase ilv5 | *Saccharomyces cerevisiae* S288c chromosome XII |

TABLE 4-continued

Examples of the keto acid reductoisomerases, which can be used to convert 2-acetolactate into 2,3-dihydroxyvalerate.

| Gene Name | Microrganismo |
| --- | --- |
| Keto acid reductoisomerase ilvC | *Campylobacter jejuni* RM1221 |
| Keto acid reductoisomerase ilvC | *Methylococcus capsulatus* str. Bath |
| Keto acid reductoisomerase ilvC | *Shewanella oneidensis* MR-1 |
| Keto acid reductoisomerase ilvC | *Dehalococcoides ethenogenes* 195 |
| Keto acid reductoisomerase ilvC | *Carboxydothermus hydrogenoformans* Z-2901 |
| Keto acid reductoisomerase ilvC | *Listeria monocytogenes* serotype 4b str. F2365 |
| Keto acid reductoisomerase ilvC | *Geobacter sulfurreducens* PCA |
| Keto acid reductoisomerase ilvC | *Streptomyces avermitilis* MA-4680 |
| Keto acid reductoisomerase ilvC | *Pseudomonas aeruginosa* PAO1 |

The terms "dihydroxy acid dehydratase", "dihydroxyacid dehydratase", "acetohydroxyacid dehydratase", "alpha, beta-dihydroxyacid dehydratase", "DHAD", "2,3-dihydroxyisovalerate dehydratase", "alpha,beta-dihydroxyisovalerate dehydratase" and "2,3-dihydroxy-acid hydro-lyase" (EC 4.2.1.9) refer to a polypeptide having catalytic activity, wherein the catalytic activity includes converting 2,3-dihydroxyvalerate into ketoisovalerate. However, there may exist other enzymes that are not classified in this group of enzymes that catalyze the conversion reaction of 2,3-dihydroxyvalerate into ketoisovalerate. Such enzymes will be considered as analogues of dihydroxy acid dehydratase. Examples of enzymes that can catalyze the conversion reaction 2,3-dihydroxyvalerate into ketoisovalerate are described in Table 5. The enzyme described in Table 5 are shown for reference only, since there are many databases in which examples of these enzymes can be found, such as GeneBank, Kyoto Encyclopedia of Genes and Genomes, Braunschweig Enzyme Database, etc.

TABLE 5

Examples of the dihydroxy acid dehydratases, which can be used to convert 2,3-dihydroxyvalerate into ketoisovalerate.

| Gene Name | Organismo |
| --- | --- |
| Dihydroxy acid dehydratase ILV3 | *Saccharomyces cerevisiae* S288c |
| Dihydroxy acid dehydratase IlvD | *Shewanella oneidensis* MR-1 |
| Dihydroxy acid dehydratase ilvD | *Ruegeria pomeroyi* DSS-3 |
| Dihydroxy acid dehydratase ilvD | *Escherichia coli* O157:H7 str. EDL933 |
| Dihydroxy acid dehydratase ilvD | *Escherichia coli* UTI89 |
| Dihydroxy acid dehydratase ilvD | *Escherichia coli* CFT073 |
| Dihydroxy acid dehydratase ilvD | *Escherichia coli* BW2952 |
| Dihydroxy acid dehydratase ilvD | *Campylobacter jejuni* RM1221 |
| Dihydroxy acid dehydratase ilvD | *Dehalococcoides ethenogenes* 195 |
| Dihydroxy acid dehydratase ilvD | *Methylococcus capsulatus* str. Bath |
| Dihydroxy acid dehydratase ilvD | *Pseudomonas syringae* pv. tomato str. DC3000 |
| Dihydroxy acid dehydratase ilvD | *Geobacter sulfurreducens* PCA |
| Dihydroxy acid dehydratase ilvD | *Listeria monocytogenes* serotype 4b str. F2365 |
| Dihydroxy acid dehydratase ilvD | *Staphylococcus aureus* subsp. *aureus* N315 |
| Dihydroxy acid dehydratase ilvD | *Yersinia pestis* Nepal516 |

The term "keto acid decarboxylase", "branched-chain-2-oxoacid decarboxylase", "branched-chain oxo acid decarboxylase", "branched-chain alpha-keto acid decarboxylase", "branched-chain keto acid decarboxylase" (EC 4.1.1.72) refer to a polypeptide having catalytic activity, wherein the catalytic activity includes converting ketoisovalerate into isobutyraldehyde. However, there may exist other enzymes that are not classified in this group of enzymes that catalyze the conversion reaction of ketoisovalerate into isobutyraldehyde. Such enzymes will be considered as analogues of keto acid decarboxylase. Examples of the enzymes that can catalyze the conversion reaction from ketoisovalerate into isobutyraldehyde are described in Table 6. The enzymes described in Table 6 are shown for reference only, since there are many databases in which more examples of these enzymes can be found, such as GeneBank, Kyoto Encyclopedia of Genes and Genomes, Braunschweig Enzyme Database, etc.

TABLE 6

Examples of the keto acid decarboxylases, which can be used to convert ketoisovalerate into isobutyraldehyde.

| Gene Name | Microorganismo |
|---|---|
| Keto acid decarboxylase kivD | *Lactococcus lactis* subsp. *lactis* KF147 |
| Keto acid decarboxylase ipdc | *Francisella tularensis* subsp. *tularensis* TIGB03 |
| Keto acid decarboxylase pdc | *Mycobacterium smegmatis* str. MC2 155 |
| Keto acid decarboxylase BN843_1930 | *Staphylococcus aureus* M1 |
| Keto acid decarboxylase MIP_01423 | *Mycobacterium indicus pranii* MTCC 9506 |
| Keto acid decarboxylase PSYCG_05060 | *Psychrobacter* sp. G |
| Keto acid decarboxylase BB2000_0373 | *Proteus mirabilis* BB2000 |
| Keto acid decarboxylase MKAN_09665 | *Mycobacterium kansasii* ATCC 12478 |
| Keto acid decarboxylase DIN4 E1 beta | *Arabidopsis thaliana* chromosome 3 |
| Keto acid decarboxylase SLGD_00204 | *Staphylococcus lugdunensis* HKU09-01 |
| Keto acid decarboxylase ETAF_1742 | *Edwardsiella tarda* FL6-60 |
| Keto acid decarboxylase MPD5_0448 | *Melissococcus plutonius* DAT561 chromosome 1 |
| Keto acid decarboxylase | *Yersinia enterocolitica* subsp. *palearctica* Y11 |
| Keto acid decarboxylase ST548_p8192 | *Enterobacter aerogenes* EA1509E |
| Keto acid decarboxylase RTCIAT899_CH13570 | *Rhizobium tropici* CIAT 899 |

The terms "alcohol dehydrogenase", "aldehyde reductase", "ADH", "alcohol dehydrogenase (NAD)", "aliphatic alcohol dehydrogenase", "NAD-dependent alcohol dehydrogenase", "NADH-alcohol dehydrogenase" and "NADH-aldehyde dehydrogenase" (EC 1.1.1.1) refer to a polypeptide having catalytic activity, wherein the catalytic activity includes converting the compound isobutyraldehyde into isobutanol using NADH. However, there may exist other enzymes that are not classified in this group of enzymes that catalyze the conversion reaction of isobutyraldehyde into isobutanol. Such enzymes will be considered as analogues of alcohol dehydrogenase. Examples of these enzymes that can catalyze the conversion reaction of isobutyraldehyde into isobutanol using NADH are described in Table 7. The enzymes described in Table 7 are shown for reference only, since there are many databases where more examples of these enzymes can be found, such as GeneBank, Kyoto Encyclopedia of Genes and Genomes, Braunschweig Enzyme Database, etc.

TABLE 7

Examples of the alcohol dehydrogenases, which can be used to convert isobutyraldehyde into isobutanol using NADH.

| Gene Name | Microorganism |
|---|---|
| Alcohol dehydrogenase adhE | *Escherichia coli* str. BL21 DE3 |
| Alcohol dehydrogenase ZMO1596 | *Zymomonas mobilis* subsp. *mobilis* ZM4 |
| Alcohol dehydrogenase Deba_0709 | *Desulfarculus baarsi* |
| Alcohol dehydrogenase adhB | *Vibrio nigripulchritudo* |
| Alcohol dehydrogenase Sbal678_1379 | *Shewanella baltica* OS678 |
| Alcohol dehydrogenase SCV20265_3141 | *Pseudomonas aeruginosa* SCV20265 |

TABLE 7-continued

Examples of the alcohol dehydrogenases, which can be used to convert isobutyraldehyde into isobutanol using NADH.

| Gene Name | Microorganism |
|---|---|
| Alcohol dehydrogenase Shew185_1312 | *Shewanella baltica* OS185 |
| Alcohol dehydrogenase yiaY | *Desulfovibrio piezophilus* |

TABLE 7-continued

Examples of the alcohol dehydrogenases, which can be used to convert isobutyraldehyde into isobutanol using NADH.

| Gene Name | Microorganism |
|---|---|
| Alcohol dehydrogenase ERE_02800 | *Eubacterium rectale* M104/1 |
| Alcohol dehydrogenase Thethe_02115 | *Thermoanaerobacterium thermosaccharolyticum* M0795 |
| Alcohol dehydrogenase Ilyop_0504 | *Ilyobacter polytropus* |
| Alcohol dehydrogenase RradSPS_2073 | *Rubrobacter radiotolerans* |
| Alcohol dehydrogenase yiaY | *Escherichia coli* K-12 W3110 |
| Alcohol dehydrogenase Dd1591_1857 | *Dickeya zeae* |
| Alcohol dehydrogenase eutG | *Mannheimia succiniciproducens* |

The terms "alcohol dehydrogenase", "alcohol dehydrogenase (NADP+)", "aldehyde reductase (NADPH)", "NADP-alcohol dehydrogenase", "NADP+-aldehyde reductase", "NADP+-dependent aldehyde reductase", "NADPH-aldehyde reductase", "NADPH-dependent aldehyde reductase" and "alcohol dehydrogenase (NADP)" (EC 1.1.1.2) also refer to a polypeptide having catalytic activity, wherein the catalytic activity includes converting the compound isobutyraldehyde into isobutanol using NADPH. However, there may be other enzymes that are not classified in this group of enzymes that catalyze the conversion reaction of isobutyraldehyde into isobutanol. Such enzymes will be considered as analogues of alcohol dehydrogenase. Examples of enzymes that can catalyze the conversion reaction of isobutyraldehyde into isobutanol using NADPH are described in Table 8. The enzymes described in Table 8 are shown for reference only, since there are many databases where more examples of these enzymes can be found, such as Gen-

TABLE 8

Examples of the alcohol dehydrogenases, which can be used to convert isobutyraldehyde into isobutanol using NADPH.

| Gene Name | Microorganism |
| --- | --- |
| Alcohol dehydrogenase ALDR1 | *Homo sapiens* |
| Alcohol dehydrogenase Akr1a4 | *Rattus norvegicus* |
| Alcohol dehydrogenase AKR1A1 | *Equus caballus* |
| Alcohol dehydrogenase AKR1A1 | *Pteropus alecto* |
| Alcohol dehydrogenase aldr1 | *Xenopus laevis* |
| Alcohol dehydrogenase TPHA0A00140 | *Tetrapisispora phaffii* |
| Alcohol dehydrogenase AO090003000751 | *Aspergillus oryzae* |
| Alcohol dehydrogenase cce_0782 | *Cyanothece* sp. ATCC 51142 |
| Alcohol dehydrogenase ZPR_1868 | *Zunongwangia profunda* |
| Alcohol dehydrogenase yqhD | *Escherichia coli* |
| Alcohol dehydrogenase t3084 | *Salmonella enterica* subsp. *enterica* serovar Typhi Ty2 |
| Alcohol dehydrogenase SeHA_C3413 | *Salmonella enterica* subsp. *enterica* serovar Heidelberg SL476 |
| Alcohol dehydrogenase BN855_32420 | *Salmonella enterica* subsp. *enterica* serovar Bovismorbificans |
| Alcohol dehydrogenase W5S_0390 | *Pectobacterium* sp. SCC3193 |
| Alcohol dehydrogenase VCM66_A0660 | *Vibrio cholerae* M66-2 |

One aspect of the present invention relates to a method in which a multi-enzyme system sequentially produces isobutanol from lactate, and in which the production of isobutanol is associated with a $NAD^+$/NADH and/or $NADP^+$/NADPH regeneration system (FIG. 1). This conversion can be performed in a container or reactor where the entire process can be carried out continuously, semi-continuously or in a batch manner.

Moreover, preferably, the present invention overcomes the deficiencies of the prior art by providing polypeptides that convert lactate into isobutanol sequentially, with an experimental yield less than or equal to the theoretical yield.

Furthermore, the present invention may not require the quantities established by the stoichiometric reactions of $NAD^+$ and/or $NADP^+$ and NADH and/or NADPH to perform the process described above; since the method of the present invention may allow the regeneration of $NAD^+$/NADH and/or $NADP^+$/NADPH during the conversion of lactate into pyruvate and the conversion of acetolactate into 2,3-dihydroxyvalerate and the conversion of isobutyraldehyde into isobutanol.

Likewise, the process of the present invention may employ unit operations which recycle the $NAD^+$, $NADP^+$, NADH and/or NADPH system, allowing that a smaller amount of those compounds than those established by the stoichiometry may be required to convert higher amounts of lactate into isobutanol.

The present invention may use the enzymes: L-Lactate dehydrogenase (EC 1.1.1.27), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), and alcohol dehydrogenase (EC 1.1.1.1) and its analogues to convert L-lactic acid into isobutanol, wherein the amount of $NAD^+$ added to the system may be less than the amount established by the stoichiometric reaction for the conversion of L-lactate into isobutanol. The experimental yield obtained in the conversion of L-lactate into isobutanol may be less than or equal to the theoretical yield (0.411 grams of isobutanol per gram of L-lactate).

In yet another aspect, the present invention may use the enzymes: D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.1) and its analogues to convert D-lactic acid into isobutanol, wherein the amount of $NAD^+$ added to the system may be less than the amount established by the stoichiometric reaction for the conversion of D-lactate into isobutanol. The experimental yield obtained in the conversion of D-lactate into isobutanol may be less than or equal to the theoretical yield (0.411 grams of isobutanol per gram of D-lactate).

In yet another aspect, the present invention may use the enzymes: L-lactate dehydrogenase (EC 1.1.1.27), D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.1) and/or its analogues to convert a mixture of L-lactic acid and D-lactic acid into isobutanol, wherein the amount of $NAD^+$ added to the system may be less than the amount established by the stoichiometric reaction for the conversion of mixed solution of L-lactate and D-lactate into isobutanol. The experimental yield obtained in the conversion of the mixture of L-lactate and D-lactate into isobutanol may be less than or equal to the theoretical yield (0.411 grams of isobutanol per gram of mixture of L-lactate and D-lactate).

Also, the present invention may use the enzymes: L-lactate dehydrogenase (EC 1.1.1.27), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.2) and/or its analogues to convert L-lactic acid into isobutanol, wherein the amount of $NADP^+$ added to the system may be less than the amount established by the stoichiometric reaction for the conversion of L-lactate into isobutanol. The experimental yield obtained in the conversion of L-lactate into isobutanol may be less than or equal to the theoretical yield (0.411 grams of isobutanol per gram of L-lactate).

Similarly, the present invention may use the enzymes: D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.2) and/or its analogues to convert D-lactic acid into isobutanol, wherein the amount of $NADP^+$ added to the system may be less than the amount established by the stoichiometric reaction for the conversion of D-lactate into isobutanol. The experimental yield obtained for the conversion of D-lactate into isobutanol may be less than or equal to the theoretical yield (0.411 grams of isobutanol per gram of D-lactate).

On other hand, the present invention may use the enzymes: L-lactate dehydrogenase (EC 1.1.1.27), D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.2) and/or its analogues to convert a mixture of L-lactic acid and D-lactic acid into isobutanol, wherein the amount of $NADP^+$ added to the system may be less than the amount established by the stoichiometric reaction for the conversion of the mixture of L-lactate and D-lactate into isobutanol. The experimental yield obtained for the conversion of the mixture of L-lactate and D-lactate into isobutanol may be less than or equal to the theoretical yield (0.411 grams of isobutanol per gram of mixture of L-lactate and D-lactate).

Other aspects of the present invention relates to a mixture of enzymes that perform a series of reactions producing isobutanol from lactate sequentially. In turn, the preferred enzyme mixtures used to convert lactate into isobutanol are as follows:

a) When the starting substrate is L-lactate and the redox reactions use $NAD^+$/NADH to obtain isobutanol as the final product, the enzyme mixture may include L-lactate dehydrogenase (EC 1.1.1.27), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.1) and/or any of their analogues;

b) When the starting substrate is D-lactate and the redox reactions use $NAD^+$/NADH to obtain isobutanol as the final product, the enzyme mixture may include D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.1) and/or any of their analogues;

c) When the starting substrate is a mixture of L-lactate and D-lactate and the redox reactions use $NAD^+$/NADH to obtain isobutanol as the final product, the enzyme mixture may include L-lactate dehydrogenase (EC 1.1.1.27), D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.1) and/or any of their analogues;

d) When the starting substrate is L-lactate and the redox reactions use $NADP^+$/NADPH to obtain isobutanol as the final product, the enzyme mixture may include L-lactate dehydrogenase (EC 1.1.1.27), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.2) and/or any of their analogues;

e) When the starting substrate is D-lactate and the redox reactions use $NADP^+$/NADPH to obtain isobutanol as the final product, the enzyme mixture may include D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.2) and/or any of their analogues;

f) When the starting substrate is a mixture of L-lactate and D-lactate and the redox reactions use $NADP^+$/NADPH to obtain isobutanol as the final product, the enzyme mixture may include L-lactate dehydrogenase (EC 1.1.1.27), D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72) and alcohol dehydrogenase (EC 1.1.1.2) and/or any of their analogues;

g) When the starting substrate L-lactate and the redox reactions use a mixture of $NAD^+$/NADH and $NADH^+$/NADPH to obtain isobutanol as the final product, the enzyme mixture may include L-lactate dehydrogenase (EC 1.1.1.27), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.1) and alcohol dehydrogenase (EC 1.1.1.2), and/or any of their analogues;

h) When the starting substrate is D-lactate and the redox reactions use $NAD^+$/NADH and $NADP^+$/NADPH to obtain isobutanol as the final product, the enzyme mixture may include D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.1) and alcohol dehydrogenase (EC 1.1.1.2), and/or any of their analogues; and i) When the starting substrate is a mixture of L-lactate and D-Lactate and the redox reactions use $NAD^+$/NADH and $NADP^+$/NADPH to obtain isobutanol as the final product, the enzyme mixture may include L-lactate dehydrogenase (EC 1.1.1.27), D-lactate dehydrogenase (EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.1) and alcohol dehydrogenase (EC 1.1.1.2) and/or any of their analogues.

In another aspect of the present invention, a process for producing isobutanol from lactate is provided, associated with a $NAD(P)^+$/NAD(P)H regeneration system, wherein the operation mode is preferably in continuous, using free enzymes. The mixture of enzymes may be any of those above mentioned.

In a preferred aspect of the present invention, the method may include several stages described below:

I. In a mixing tank, water, lactate, a mixture of enzymes, $NAD(P)^+$/NAD(P)H, cofactor(s) and coenzyme(s) used by the enzymes to carry out the catalysis, are mixed together. The cofactor(s) and coenzyme(s) that are used by each enzyme to carry out the catalysis may be related to the nature of each enzyme. Table 9 shows some of the cofactors and the different enzymes that are preferably used in the present invention. The cofactors and coenzymes shown in Table 9 are for exemplary purposes only and do not exempt other cofactors or coenzymes to be found by a person skilled in the art.

The ingredients described above may be mixed in a pipe, a reactor, or any other container suitable to mix the ingredients.

The ingredients may be mixed by any appropriate method to promote interaction between the enzyme(s) and the substrate(s). In addition, the mixing may be carried out mechanically, pneumatically, or hydraulically. A single mixing method may be utilized, or a two or more different mixing methods may be combined to mix the ingredients.

II. The mixture prepared in I is subjected to catalytic reactions. The effluent stream of the mixing tank continuously passes through a reactor such that the reaction conditions, including catalytic reaction conditions, remain stable with a pH of between 2 and 12, between 4 and 10, preferably between 6 and 8, and a temperature of between 5° C. and 50° C., preferably between 15° C. and 40° C., more preferably between 25° C. and 37° C. When the effluent stream enters the reactor, isobutanol may be produced from lactate with a conversion efficiency equal to or less than 100%. Preferably, the duration of the catalytic reactions is sufficiently long to convert lactate into isobutanol.

In one aspect of the present invention, during such procedure, lactate may catalytically convert into isobutanol. The catalytic conversions of lactate may be conducted in a container that is suitable to carry out the catalytic conversion. For example, a stirred tank reactor, a plug flow reactor, a fluidized bed reactor, or a packed bed reactor, may be used alone or in combination.

III. Isobutanol is separated from the reactant obtained in II. A reactor outlet stream, which may be enriched with isobutanol and depleted in lactate, passes through a separation system wherein the cofactors, coenzymes and enzymes can be separated from isobutanol and water. The enzymes, coenzymes and cofactors may form a concentrated stream, which can be recycled to the mixing tank in I or reactor in II. The separation may be done by any method suitable to separate molecules based on, for example, their physicochemical properties.

IV. On the other hand, the water-isobutanol mixture may be separated by another system. Any separation methods that are suitable to separate molecules may be employed. The separation may be conducted based on a size of the molecules. The separation systems may be: system of membranes (reverse osmosis, pervaporation, nanofiltration, ultrafiltration, etc.), distillation, evaporation or any other system which allows the separation of molecules either by size or by any of their physicochemical properties.

When separating isobutanol, the reactant obtained by the catalytic conversions may be separated into a stream including isobutanol and water, and a stream including components other than isobutanol and water. The stream including isobutanol and water may further be separated into a stream including isobutanol and a stream including water. The stream including components other than isobutanol and water may be recycled by mixing into in the mixing tank or the reactor.

TABLE 9

Cofactors and coenzymes used by the enzymes, which compose the enzyme mixture.

| Enzyme Name | Origin | Cofactor | Co-enzyme |
|---|---|---|---|
| Acetolactate synthase | Nicotiana tabacum | $Mg^{2+}$ | FAD, ThPP |
| Acetolactate synthase | Mycobacterium tuberculosis | $Mg^{2+}$ | FAD, ThPP |
| Acetolactate synthase | E. coli | $Mg^{2+}$ $K^+$ | FAD, ThPP |
| Acetolactate synthase | Bacillus subtilis | $Mg^{2+}$ | FAD |
| Acetolactate synthase | S. cerevisiae | $Mg^{2+}$ | |
| Acetolactate synthase | Methanococcus aeolicus | $Mg^{2+}$, $Mn^{2+}$ | FAD, FMN, ThPP |
| Acetolactate synthase | Methanococcus voltae | | ThPP |
| Ketoacid reductoisomerase | Oryza sativa | $Mg^{2+}$ | |
| Ketoacid reductoisomerase | Corynebacterium glutamicum | $Mg^{2+}$ | |
| Ketoacid reductoisomerase | Spinacia oleracea | $Mg^{2+}$ | |
| Ketoacid reductoisomerase | Hordeum vulgare | $Mg^{2+}$ | |
| Ketoacid reductoisomerase | Neurospora crassa | $Mg^{2+}$ | |
| Ketoacid reductoisomerase | Salmonella enterica | $Mg^{2+}$ | |
| Di-Hydroxyacid of hydratase | Spinacia oleracea | $Co^{2+}$, $Fe^{2+}$, $Mg^{2+}$, $Mn^{2+}$ | |
| Di-Hydroxyacid of hydratase | Sulfolobus solfataricus | $Mn^{2+}$ | |
| Di-Hydroxyacid of hydratase | Neurospora crassa (micelio) | $Mg^{2+}$ | |
| Di-Hydroxyacid of hydratase | Methanococcus aeolicus | $Co^{2+}$, $Fe^{2+}$, $Mg^{2+}$, $Mn^{2+}$ | |
| Di-Hydroxyacid of hydratase | Escherichia coli | $Fe^{2+}$, $Mg^{2+}$, $Mn^{2+}$ | |
| Keto acid decarboxylase | Lactococcus lactis | | ThPP |
| Alcohol dehydrogenase | Oenococcus oeni | $Mg^{2+}$, $Na^+$, $Ni^{2+}$ | |
| Alcohol dehydrogenase | Oenococcus oeni | $Mg^{2+}$, $Na^+$, $Ni^{2+}$ | |
| Alcohol dehydrogenase | Saccharomyces cerevisiae | $Co^{2+}$, $Zn^{2+}$ | |
| Alcohol dehydrogenase | Geobacillus thermodenitrificans | $Fe^{2+}$, $Na^{2+}$ | |
| Alcohol dehydrogenase | Saimiri sciureus | $Zn^{2+}$ | |
| Alcohol dehydrogenase | Acetobacter pasteurianus SKU1108 | $Zn^{2+}$, $NAD^+$ | |
| Alcohol dehydrogenase | Natronomonas pharaonis | $K^+$, $Na^+$ | |
| Alcohol dehydrogenase | Emericella nidulans | $Zn^{2+}$ | |
| Alcohol dehydrogenase | Flavobacterium frigidimaris KUC-1 | $Zn^{2+}$ | |
| Alcohol dehydrogenase | Desulfovibrio gigas | $Zn^{2+}$ | |
| Alcohol dehydrogenase | Saccharomyces cerevisiae | $Zn^{2+}$ | |

In a different aspect of the present invention, a method for producing isobutanol from lactate is provided, in which the production of isobutanol is associated with a regeneration system of $NAD(P)^+/NAD(P)H$. Preferably, the operation mode is in continuous, and use a mixture of immobilized enzymes. The mixture of immobilized enzymes may include any of those described above. The immobilization can be done by different methods generally known in the art. Table 10 shows some of the carriers that may be used to immobilize enzymes. The carriers listed in Table 10 are exemplary purposes only and do not exempt other carriers to be found by a person skilled in the art even if not mentioned in Table 10.

TABLE 10

Carriers used to immobilize enzymes.

| Carrier | Enzyme | Reference |
|---|---|---|
| Calcium Alginate | Lipasa | Wona et al., 2005 |
| Silica Gel | Peroxidase | Lia et al., 1996 |
| Zeolite | Glucose Oxidase | Liu et al., 1997 |
| Perlite | Cholesterol Oxidase | Torabi et., al 2007 |

The method may include several stages as described below:

I. In a tank, enzymes are immobilized in/on a carrier. One or more enzymes can be immobilized in/on the same or different carriers. Additionally, the carriers may be of the same type with different number of enzymes, or the carriers may be of different types, have different sizes, or have different chemical compositions. Each carrier may contain one or more kind of enzymes. Coenzymes and cofactors may or may not present in/on the carrier. Once the enzymes are immobilized, these enzymes will be added to the reactor.

II. In a separate mixing tank, water, lactate and $NAD(P)^+$/$NAD(P)H$ are mixed. Each enzyme may use cofactor(s) and coenzyme(s) to perform catalysis, depending on the nature of the enzyme. Table 9 shows some coenzymes and cofactors that are preferably used with various enzymes in the present invention. Cofactors and coenzymes described in Table 9 are for exemplary purposes only and do not exempt other cofactors and coenzymes to be found by a person skilled in the art.

The ingredients described above may be mixed in a pipe, a reactor, or any other container appropriate to mix the ingredients.

The ingredients may be mixed by any appropriate methods to promote interaction between the enzyme(s) and the substrate(s). In addition, the mixing may be carried out mechanically, pneumatically, or hydraulically. A single mixing method may be utilized, or a two or more different mixing methods may be combined to mix the ingredients.

III. The stream exiting stage II flows continuously through a reactor containing the immobilized enzymes. The reactor maintains stable reaction conditions with a pH of between 2 and 12, between 4 and 10, preferably between 6 to 8, and a temperature of between 5° C. and 50° C., preferably between 15° C. and 40° C., more preferably between 25° C. and 37° C. When the stream enters the reactor, isobutanol may be produced from lactate with a conversion efficiency equal to or less than 100%. Preferably the carrier should be maintained within the reactor. However, the carrier may be removed from the reactor and may be recycled for further use.

IV. The output enriched in isobutanol and lactate depleted effluent from stage III, may pass through a separation system, wherein the coenzymes and cofactors are separated from isobutanol and water. Coenzymes and cofactors may be lead to a concentrated stream that may be recycled to the mixing tank or to the enzyme reactor.

V. The isobutanol-water mixture exiting the separation system described in IV, may be separated by other separation system. This system may produce two streams, in one hand an isobutanol stream and on the other hand a water stream.

The separation systems mentioned in IV and V may include: membrane systems (reverse osmosis, pervaporation, nanofiltration, ultrafiltration, etc.), distillation, evaporation or any other system which allows the separation of molecules by either size or by any of their physicochemical properties.

One aspect of the present invention relates to a biofuel or biofuel precursor prepared by the process disclosed above. The biofuel or biofuel precursor preferably meets requirements of ASTM D7862.

Another aspect of the present invention relates to an automotive fuel prepared by blending a mixture of hydrocarbons and the biofuel precursor described above.

EXAMPLES

The following examples are intended to clarify the novelty of the present invention. It should be understood that the following examples are not a limitation to the scope of the present invention. From the description of the invention and from the following examples, a person skilled in the art may carry out some modifications, which will be considered within the scope and spirit of the invention as it is described in the claims.

Example 1. Quantification of Enzymatic Activity

To determine the enzymatic activity of various enzymes, different enzyme genes were cloned into commercial expression vectors, such as the DUET (Merck, USA) series, by following the protocols described in Green and Sambrook, 2010. Subsequently, the enzymes were purified according to protocols described in Green and Sambrook, 2010. A list of enzymes tested is shown in Table 11.

TABLE 11

Enzymes used to demonstrate the present invention.

| Enzime | Microorganism | Substrate | Product |
|---|---|---|---|
| L-LDH (EC 1.1.1.27) | *Escherichia coli* APEC O1 | L-Lactate | Pyruvate |
| L-LDH (EC 1.1.1.27) | *Lactococcus lactis* subsp. *lactis* Il1403 | L-Lactate | Pyruvate |
| L-LDH (EC 1.1.1.27) | *Streptococcus pneumoniae* AP200 | L-Lactate | Pyruvate |
| D-LDH (EC 1.1.1.28) | *Escherichia coli* K-12 MG1655 | D-Lactate | Pyruvate |
| D-LDH (EC 1.1.1.28) | *Pseudomonas aeruginosa* RP73 | D-Lactate | Pyruvate |
| D-LDH (EC 1.1.1.28) | *Planctomyces brasiliensis* | D-Lactate | Pyruvate |
| ALS (EC 2.2.1.6) | *Escherichia coli* str. K-12 MG1655 | Pyruvate | 2AL |
| ALS (EC 2.2.1.6) | *Bacillus subtilis* subsp. *subtilis* str. 168 | Pyruvate | 2AL |
| ALS (EC 2.2.1.6) | *Saccharomyces cerevisiae* S288c | Pyruvate | 2AL |
| CAR (EC 1.1.1.86) | *Escherichia coli* K-12 MG1655 | 2AL | DHV |
| CAR (EC 1.1.1.86) | *Corynebacterium glutamicum* ATCC 13032 | 2AL | DHV |
| DAD (EC 4.2.1.9) | *Escherichia coli* UTI89 | DHV | KIV |
| DAD (EC 4.2.1.9) | *Staphylococcus aureus* subsp. *aureus* N315 | DHV | KIV |
| CAD (EC 4.1.1.72) | *Staphylococcus aureus* M1 | KIV | IBA |
| CAD (EC 4.1.1.72) | *Lactococcus lactis* subsp. *lactis* KF147 | KIV | IBA |
| CAD (EC 4.1.1.72) | *Arabidopsis thaliana* | KIV | IBA |
| ADH (EC 1.1.1.1) | *Escherichia coli* BL21 DE3 | IBA | IBOH |
| ADH (EC 1.1.1.1) | *Zymomonas mobilis* subsp. *mobilis* ZM4 | IBA | IBOH |
| ADH (EC 1.1.1.1) | *Escherichia coli* K-12 W3110 | IBA | IBOH |
| ADH (EC 1.1.1.2) | *Escherichia coli* K12 W3110 | IBA | IBOH |
| ADH (EC 1.1.1.2) | *Rattus norvegicus* | IBA | IBOH |
| ADH (EC 1.1.1.2) | *Homo sapiens* | IBA | IBOH |

Notes.
L-LDH: L-lactate dehydrogenase; D-LDH: D-lactate dehydrogenase; ALS: acetolactate synthase; CAR: keto acid reductoisomerase; DAD: dihydroxy acid dehydratase; CAD: keto acid decarboxylase; ADH: alcohol dehydrogenase; 2AL 2-acetolactate; DHV 2,3-dihydroxyvalerate; KIV: ketoisovalerate; IBA: isobutyraldehyde; IBOH: isobutanol.

Enzymatic assays and results are described below:
a) L-Lactate Dehydrogenase (EC 1.1.1.27):

The L-lactate dehydrogenase converts L-lactate into pyruvate using $NAD^+$ and/or $NADP^+$, therefore the assays were conducted by varying the initial concentrations of L-lactate, NAD$^+$ and/or NADP$^+$, pH and temperature, following the protocols described in literature (Cetinel et al., 2013). Three enzymes from different microorganisms were used as an example. L-Lactate consumption kinetics was monitored by HPLC with a refractive index detector by using a Rezex-ROA organic acids H$^+$ column. The production of NADH and/or NADPH was monitored using a Cary-60 spectrophotometer with temperature control at a wavelength of 340 nm. The test conditions are shown in Table 12.

TABLE 12

Reaction conditions tested for the enzyme L-lactate dehydrogenase (EC 1.1.1.27).

| Variable | Assay Conditions |
|---|---|
| pH | 2, 5, 7, 10 and 12 |
| Temperature (° C.) | 5, 15, 25, 35, 45 and 55 |
| L-Lactate (g/L) | 1, 50, 100, 200, 300 |
| NAD$^+$ and/or NADP$^+$ (g/L) | 1, 5 and 10 |

In all assays, both conversions from L-lactate into pyruvate and NADH and/or NADPH production were observed. The results shown in Table 13 represent the conversion efficiency obtained after one hour of reaction time, considering the stoichiometry of the reaction reported by different international databases such as Kyoto Encyclopedia of Genes and Genomes and Braunschweig Enzyme Database.

TABLE 13

Conversion of L-lactate to pyruvate by L-lactate dehydrogenase enzymes (EC 1.1.1.27).

| Higher Conversion | Conditions | Lower Conversion | Conditions |
|---|---|---|---|
| 1. L-LDH of *Escherichia coli* APEC O1 | | | |
| Greater than 98% | pH (7), Temp (35° C.), NAD$^+$ and/or NADP$^+$ (5 g/L), L-lactate (100 g/L) | Less than 2% | pH (2), Temp (5° C.), NAD$^+$ and/or NADP$^+$ (1 g/L) L-lactate (200 g/L) |
| 2. L-LDH of *Lactobacillus lactis* subsp. *lactis* Il1403 | | | |
| Greater than 96% | pH (7), Temp (35° C.), NAD$^+$ and/or NADP$^+$ (10 g/L) L-lactate (300 g/L) | Less than 1% | pH (2), Temp (55° C.), NAD$^+$ and/or NADP$^+$ (1 g/L) L-lactate (300 g/L) |
| 3. L-LDH of *Streptococcus pneumoniae* AP200 | | | |
| Greater than 99% | pH (7), Temp (25° C.), NAD$^+$ and/or NADP$^+$ (1 g/L) L-lactate (200 g/L) | Less than 5% | pH (12), Temp (55° C.), NAD$^+$ and/or NADP$^+$ (1 g/L) L-lactate (300 g/L) | b) D-Lactate Dehydrogenase (EC 1.1.1.28)

The D-lactate dehydrogenase converts D-lactate into pyruvate using NAD$^+$ and/or NADP$^+$, therefore the assays were conducted by varying the initial concentrations of D-lactate, NAD$^+$ and/or NADP$^+$, pH and temperature, following the protocols described in literature (Kim et al., 2014). Three enzymes from different microorganisms were used as an example. D-Lactate consumption kinetics were monitored by HPLC with a refractive index detector using a Rezex-ROA organic acids H$^+$ column; NADH and/or NADPH production was monitored using a Cary-60 spectrophotometer with temperature control at a wavelength of 340 nm. The assay conditions are shown in Table 14.

TABLE 14

Reaction conditions assayed for the enzyme D-lactate dehydrogenase (EC 1.1.1.28).

| Variable | Assay Conditions |
|---|---|
| pH | 2, 5, 7, 10 and 12 |
| Temperature (° C.) | 5, 15, 25, 35, 45 and 55 |
| D-Lactate (g/L) | 1, 50, 100, 200, 300 |
| NAD$^+$ and/or NADP$^+$ (g/L) | 1, 5 and 10 |

In all performed assays, conversion from D-lactate to pyruvate and the production of NADH and/or NADPH were observed. The results shown in Table 15 represent the conversion efficiency obtained after one hour of reaction time, considering the stoichiometry of the reaction reported by different international databases such as Kyoto Encyclopedia of Genes and Genomes and Braunschweig Enzyme Database.

TABLE 15

Conversion of D-lactate to pyruvate by D-lactate dehydrogenase enzyme (EC 1.1.1.28).

| Higher Conversion | Conditions | Lower Conversion | Conditions |
|---|---|---|---|
| 1. D-LDH of *Escherichia coli* K-12 MG1655 | | | |
| Greater than 98% | pH (7), Temp (35° C.), NAD$^+$ and/or NADP$^+$ (5 g/L), D-lactate (100 g/L) | Less than 2% | pH (2), Temp (5° C.), NAD$^+$ and/or NADP$^+$ (1 g/L) D-lactate (200 g/L) |
| 2. D-LDH of *Pseudomonas aeruginosa* RP73 | | | |
| Greater than 96% | pH (7), Temp (35° C.), NAD$^+$ and/or NADP$^+$ (10 g/L) D-lactate (300 g/L) | Less than 1% | pH (2), all temperatures, NAD$^+$ and/or NADP$^+$ (1 g/L), D-lactate (300 g/L) |
| 3. D-LDH of *Planctomyces brasiliensis* | | | |
| Greater than 99% | pH (7), Temp (25° C.), NAD$^+$ and/or NADP$^+$ (1 g/L) D-lactate (200 g/L) | Less than 5% | pH (2), Temp (55° C.), NAD$^+$ and/or NADP$^+$ (1 g/L) D-lactate (300 g/L) | c) Acetolactate Synthase (EC 2.2.1.6)

Acetolactate synthase converts pyruvate into 2-acetolactate, therefore, the assays were conducted by varying the initial concentrations of pyruvate, pH and temperature, following the protocols described in the literature (Holtzclaw and Chapman, 1975; Barak et al., 1987; Atsumi et al., 2009). Three enzymes from different microorganisms were used as an example. Pyruvate consumption kinetics were monitored by UHPLC with a UV detector at a wavelength of 210 nm using an Acclaim organic acids column, a Cary-60 spectrophotometer was also used with temperature control to a wavelength of 320 nm. The assay conditions are shown in Table 16.

TABLE 16

Reaction conditions assayed for acetolactate synthase enzyme (EC 2.2.1.6).

| Variable | Assay conditions |
|---|---|
| pH | 2, 5, 7, 10 and 12 |
| Temperature (° C.) | 5, 15, 25, 35, 45 and 55 |
| Pyruvate (g/L) | 1, 25, 50 and 100 |

Table 17 shows the results of the conversion efficiency obtained after one hour of reaction time considering the stoichiometry of the reaction reported by different international databases, such as Kyoto Encyclopedia of Genes and Genomes and Braunschweig Enzyme Database.

TABLE 17

Conversion of pyruvate to acetolactate by acetolactate synthase enzymes (EC 2.2.1.6).

| Higher conversion | Conditions | Lower Conversion | Conditions |
|---|---|---|---|
| 1. ALS of *Escherichia coli* K-12 MG1655 | | | |
| Greater than 99% | pH (7), Temp (35° C.), Pyruvate (100 g/L) | Less than 10% | pH (5), Temp (5° C.), Pyruvate (100 g/L) |
| 2. ALS of *Bacillus subtilis* subsp. *subtilis* str. 168 | | | |
| Grater than 96% | pH (7), Temp (35° C.), Pyruvate (100 g/L) | Less than 6% | pH (10), Temp (55° C.), Pyruvate (Grater than 50 g/L) |
| 3. ALS of *Saccharomyces cerevisiae* S288c | | | |
| Grater than 99% | pH (7), Temp (35° C.), Pyruvate (100 g/L) | Less than 5% | pH (10), Temp (55° C.), Pyruvate (100 g/L) | d) Keto Acid Reductoisomerase (EC 1.1.1.86) and Dihydroxy Acid Dehydratase (EC 4.2.1.9).

On one hand, the keto acid reductoisomerase converts 2-acetolactate into 2,3-dihydroxyvalerate while dihydroxy acid dehydratase converts 2,3-dihydroxyvalerate into ketoisovalerate. Due to the non-commercial availability of 2-acetolactate and the unstability of 2,3-dihydroxyvalerate, the activities of both enzymes were determined indirectly by an assay where acetolactate synthase and keto acid reductoisomerase and dihydroxy acid dehydratase were coupled. This was accomplished by varying the initial concentrations of pyruvate, NADH and/or NADPH, such as pH and temperature using protocols described in literatures (Flint et al., 1993; Bastian et al., 2011; Li et al., 2011.). A combination of two reductoisomerase enzymes and two dihydroxy keto acid dehydratase enzymes from different microorganisms were used as an example. The pyruvate consumption kinetics and ketoisovalerate production (dihydroxy dehydratase enzyme activity) were monitored by UHPLC with a UV detector at a wavelength of 210 nm using an Acclaim organic acids column; NADH and/or NADPH consumption (substrate for the ketoacid reductoisomerase enzyme) was monitored using a Cary-60 spectrophotometer with temperature control at a wavelength of 340 nm. The assay conditions are shown in Table 18.

TABLE 18

Reaction conditions assayed for keto acid reductoisomerase (EC 1.1.1.86) and dihydroxy acid dehydratase (EC 4.2.1.9).

| Variable | Assay Conditions |
|---|---|
| pH | 2, 5, 7, 10 and 12 |
| Temperature (° C.) | 5, 15, 25, 35, 45 and 55 |
| Pyruvate (g/L) | 1, 5, 10, 15 and 25 |
| NADH and/or NADPH (g/L) | 1, 5 and 10 |

Table 19 shows the results of the conversion efficiency obtained after one hour of reaction time considering the stoichiometry of the reaction reported by different international databases, such as Kyoto Encyclopedia of Genes and Genomes and Braunschweig Enzyme Database.

TABLE 19

Conversion of pyruvate to ketoisovalerate by keto acid reductoisomerase (EC 1.1.1.86) and dihydroxy acid dehydratase (EC 4.2.1.9) enzymes.

| Higher conversion | Conditions | Lower Conversion | Conditions |
|---|---|---|---|
| 1. CAR of *Escherichia coli* K-12 MG1655 and DAD of *Escherichia coli* UTI89 | | | |
| Grater than 99% | pH (7), Temp (35° C.), NADH and/or NADPH (5 g/L), Pyruvate (25 g/L) | Less than 3% | pH (10), Temp (55° C.), NAD+ and/or NADP+ (5 g/L), Pyruvate (25 g/L) |
| 2. CAR of *Escherichia coli* K-12 MG1655 and DAD of *Staphylococcus aureus* subsp. *aureus* N315 | | | |
| Grater than 90% | pH (7), Temp (35° C.), NADH and/or NADPH (10 g/L), Pyruvate (25 g/L) | Less than 5% | pH (5), Temp (5° C.), NAD+ and/or NADP+ (1 g/L), Pyruvate (1 g/L) |
| 3. CAR of *Corynebacterium glutamicum* ATCC 13032 and DAD of *Escherichia coli* UTI89 | | | |
| Grater than 97% | pH (7), Temp (35° C.), NADH and/or NADPH (10 g/L), Pyruvate (25 g/L) | Less than 3% | pH (10), Temp (55° C.), NAD+ and/or NADP+ (1 g/L), Pyruvate (1 g/L) |
| 4. CAR of *Corynebacterium glutamicum* ATCC 13032 and DAD of *Staphylococcus aureus* subsp. *aureus* N315 | | | |
| Grater than 95% | pH (7), Temp (35° C.), NADH and/or NADPH (5 g/L), Pyruvate (25 g/L) | Less than 3% | pH (2), Temp (55° C.), NAD+ and/or NADP+ (1 g/L), Pyruvate (1 g/L) | e) Keto Acid Decarboxylase (EC 4.1.1.72)

Keto acid decarboxylase converts ketoisovalerate to isobutyraldehyde, therefore the assays were conducted by varying the initial concentrations of ketoisovalerate, pH and temperature, following the protocols described in the literature (Plaza et al. 2004). Three enzymes from different microorganisms were used as an example. Ketoisovalerate consumption kinetics were monitored by UHPLC with a UV detector at a wavelength of 210 nm using an Acclaim organic acids column, a Cary-60 spectrophotometer was also used with temperature control to a wavelength of 318 nm. The assay conditions are shown in Table 20.

TABLE 20

Reaction conditions assayed for keto acid decarboxylase enzyme (EC 4.1.1.72).

| Variable | Assay Conditions |
|---|---|
| pH | 2, 5, 7, 10 and 12 |
| Temperature (° C.) | 5, 15, 25, 35, 45 and 55 |
| Cetoisovalerate (g/L) | 1, 5, 10, 15 and 25 |

Table 21 shows the results of the conversion efficiency obtained after one hour of reaction time, considering the stoichiometry of the reaction reported by different international databases, such as Kyoto Encyclopedia of Genes and Genomes and Braunschweig Enzyme Database.

TABLE 21

Conversion of ketoisovalerate into isobutyraldehyde by keto acid decarboxylase enzyme (EC 4.1.1.72).

| Higher conversion | Conditions | Lower Conversion | Conditions |
|---|---|---|---|
| 1. CAD of *Staphylococcus aureus* M1 | | | |
| Grater than 97% | pH (7), Temp (35° C.), ketoisovalerate (15 g/L) | Less than 9% | pH (12), Temp (55° C.), ketoisovalerate (a partir de 10 g/L) |
| 2. CAD of *Lactococcus lactis* subsp. *lactis* KF147 | | | |
| Grater than 99% | pH (7), Temp (35° C.), ketoisovalerate (25 g/L) | Less than 10% | pH (12), Temp (a partir de 45° C.), ketoisovalerate (25 g/L) |
| 3. CAD of *Arabidopsis thaliana* | | | |
| Grater than 99% | pH (7), Temp (35° C.), ketoisovalerate (a partir de 1 g/L) | Less than 5% | pH (12), Temp (35° C.), ketoisovalerate (100 g/L) | f) Alcohol Dehydrogenase (EC 1.1.1.1).

This alcohol dehydrogenase converts isobutyraldehyde into isobutanol using NADH, therefore the assays were conducted by varying the initial concentrations of isobutyraldehyde, NADH, pH and temperature, following the protocols described in the literature (Atsumi et al., 2010). Three enzymes from different microorganisms were used as an example. Isobutanol production kinetics was monitored by HPLC with a refractive index detector by using a Rezex-ROA organic acids H$^+$ column, the consumption of NADH was monitored using a Cary-60 spectrophotometer with temperature control at a wavelength of 340 nm. The assay conditions are shown in Table 22.

TABLE 22

Reaction conditions assayed for alcohol dehydrogenase enzyme (EC 1.1.1.1).

| Variable | Assay Conditions |
|---|---|
| pH | 2, 5, 7, 10 and 12 |
| Temperature (° C.) | 5, 15, 25, 35, 45 and 55 |
| Isobutiraldehido (g/L) | 1, 25, 50 and 75 |
| NADH (g/L) | 1, 5 and 10 |

In all performed assays conversion from isobutyraldehyde into isobutanol and NADH consumption were observed. The results shown in Table 23 represent the conversion efficiency obtained after one hour of reaction time, considering the stoichiometry of the reaction reported by different international databases, such as Kyoto Encyclopedia of Genes and Genomes and Braunschweig Enzyme Database.

TABLE 23

Conversion of isobutyraldehyde into isobutanol by alcohol dehydrogenase enzymes (EC 1.1.1.1).

| Higher conversion | Conditions | Lower Conversion | Conditions |
|---|---|---|---|
| 1. ADH of *Escherichia coli* BL21 DE3 | | | |
| Grater than 98% | pH (7), Temp (35° C.), NADH (from 1 g/L), isobutyraldehyde (from 25 g/L) | Less than 2% | pH (2), Temp (5° C.), NADH (from 1 g/L), isobutyraldehyde (from 50 g/L) |
| 2. ADH of *Zymomonas mobilis* subsp. *mobilis* ZM4 | | | |
| Grater than 96% | pH (7), Temp (35° C.), NAD$^H$ (from 5 g/L), isobutyraldehyde (from 25 g/L) | Less than 2% | pH (2), Temp (5° C.), NADH (from 1 g/L), isobutyraldehyde (from 50 g/L) |
| 3. ADH of *Escherichia coli* K-12 W3110 | | | |
| Grater than 98% | pH (7), Temp (35° C.), NAD$^H$ (from 10 g/L), isobutyraldehyde (from 50 g/L) | Less than 2% | pH (2), Temp (5° C.), NADH (from 1 g/L), isobutyraldehyde (from 50 g/L) | g) Alcohol Dehydrogenase (EC 1.1.1.2).

The alcohol dehydrogenase converts isobutyraldehyde into isobutanol using NADPH, therefore the assays were conducted by varying the initial concentrations of isobutyraldehyde, NADPH, pH and temperature, following the protocols described in the literature (Atsumi et al., 2010). Three enzymes from different microorganisms were used as an example. Isobutanol production kinetics was monitored by HPLC with a refractive index detector by using a Rezex-ROA organic acids H$^+$ column, the consumption of NADH was monitored using a Cary-60 spectrophotometer with temperature control at a wavelength of 340 nm. The test conditions are shown in Table 24.

TABLE 24

Reaction conditions assayed for alcohol dehydrogenase enzyme (EC 1.1.1.2).

| Variable | Assay Conditions |
|---|---|
| pH | 2, 5, 7, 10 and 12 |
| Temperature (° C.) | 5, 15, 25, 35, 45 and 55 |
| Isobutiraldehido (g/L) | 1, 25, 50 and 75 |
| NADPH (g/L) | 1, 5 and 10 |

In all performed assays, conversion from isobutyraldehyde into isobutanol and NADPH consumption were observed. The results shown in Table 25 represent the conversion efficiency obtained after one hour of reaction time, considering the stoichiometry of the reaction reported by different international databases such as Kyoto Encyclopedia of Genes and Genomes and Braunschweig Enzyme Database.

TABLE 25

Conversion of isobutyraldehyde into isobutanol by alcohol dehydrogenase enzymes (EC 1.1.1.1).

| Higher conversion | Conditions | Lower Conversion | Conditions |
|---|---|---|---|
| 1. ADH of *Escherichia coli* K-12 W3110 | | | |
| Grater than 95% | pH (7), Temp (35° C.), NADPH (5 g/L), isobutyraldehyde (from 25 g/L) | Less than 2% | pH (12), Temp (55° C.), NADPH (from 1 g/L), isobutyraldehyde (from 50 g/L) |
| 2. ADH of *Rattus norvegicus* | | | |
| Grater than 96% | pH (7), Temp (35° C.), NADPH (from 5 g/L), isobutyraldehyde (from 25 g/L) | Less than 2% | pH (2), Temp (5° C.), NADPH (from 1 g/L), isobutyraldehyde (from 50 g/L) |
| 3. ADH of *Homo sapiens* | | | |
| Grater than 98% | pH (7), Temp (35° C.), NADPH (from 10 g/L), isobutyraldehyde (from 50 g/L) | Less than 2% | pH (2), Temp (5° C.), NADPH (from 1 g/L), isobutyraldehyde (from 50 g/L) |

Example 2. Enzymatic Production of Isobutanol from Lactate, Coupled with NAD$^+$/NADH and/or NADP$^+$/NADPH Regeneration System in One Batch Process This example is intended to demonstrate the NAD$^+$/NADH and/or the NADP$^+$/NADPH regeneration concept:
a) NAD$^+$/NADH, by coupling an enzyme that catalyzes a production of NADH and two enzymes that catalyze a production of NAD$^+$ according to the following reactions:
Lactate conversion into pyruvate. In this reaction two NADH molecules are obtained from two NAD$^+$ molecules, along with the conversion of two lactate molecules into two pyruvate molecules. This reaction can be performed by a L-lactate dehydrogenase enzyme (EC 1.1.1.27) and/or by D-lactate dehydrogenase enzymes (EC 1.1.1.28).

$$2C_3H_6O_3 + 2NAD^+ ==> 2C_3H_4O_3 + 2NADH + 2H^+ \quad (1)$$

Pyruvate conversion into 2-acetolactate. In this reaction, one 2-acetolactate molecule is obtained from two pyruvate molecules. This reaction can be performed by acetolactate synthase enzymes (EC 2.2.1.6):

$$2C_3H_4O_3 ==> C_5H_8O_4 + CO_2 \quad (2)$$

2-acetolactate conversion into 2,3-dihydroxyvalerate. In this reaction, one 2,3-dihydroxyvalerate molecule is obtained from one 2-acetolactate molecule along with the formation of one NAD$^+$ molecule from one NADH molecule. This reaction can be catalyzed by keto acid reductoisomerase enzymes (EC 1.1.1.86). The native enzyme has very low affinity for NADH. However, there may be mutants that use NADH as a substrate that may be known in the literature (Rane et al, 1997.). Those mutants can carry out the following reaction:

$$C_5H_8O_4 + NADH + H^+ ==> C_5H_{10}O_4 + NAD^+ \quad (3)$$

2,3-dihydroxyvalerate conversion into ketoisovalerate. In this reaction, one ketoisovalerate molecule is obtained from one 2,3-dihydroxyvalerate molecule. This reaction can be catalyzed by dihydroxy acid dehydratase enzymes (EC 4.2.1.9):

$$C_5H_{10}O_4 ==> C_5H_8O_3 + H_2O \quad (4)$$

Ketoisovalerate conversion into isobutyraldehyde. In this reaction, one isobutyraldehyde molecule is obtained from one ketoisovalerate molecule. This reaction can be catalyzed by keto acid decarboxylase enzymes (EC 4.1.1.72):

$$C_5H_8O_3 ==> C_4H_8O + CO_2 \quad (5)$$

Isobutyraldehyde conversions into isobutanol. In this reaction, one isobutanol molecule is obtained from one isobutyraldehyde molecule, along with the formation of one NAD$^+$ molecule from one NADH molecule. This reaction can be catalyzed by alcohol dehydrogenase enzymes (EC 1.1.1.1):

$$C_4H_8O + NADH + H^+ ==> C_4H_{10}O + NAD^+ \quad (6)$$

From the above chemical equations, the overall stoichiometric of the multienzymatic system has theoretically no loss or gain of NAD$^+$ or NADH. The overall reaction results in the use of two lactate molecules to produce one isobutanol molecule, obtaining 100% conversion efficiency in accordance with the following reaction:

$$2C_3H_6O_3 ==> C_4H_{10}O + 2CO_2 + H_2O \quad (7)$$

b) NADP$^+$/NADPH, by coupling an enzyme that produces NADPH and two enzymes that produce NADP$^+$ according to the following reactions:

Lactate conversion into pyruvate. In this reaction, two NADPH molecules are obtained from two NADP$^+$ molecules along with the conversion of two lactate molecules into two pyruvate molecules. This reaction can be catalyzed by a L-lactate dehydrogenase enzyme (EC 1.1.1.27) and/or by D-lactate dehydrogenase enzymes (EC 1.1.1.28):

$$2NADP^+ + 2C_3H_6O_3 ==> 2NADPH + 2C_3H_4O_3 + 2H^+ \tag{8}$$

Pyruvate conversion into 2-acetolactate. In this reaction, one 2-acetolactate molecule is obtained from two pyruvate molecules. This reaction can be catalyzed by acetolactate synthase enzymes (EC 2.2.1.6):

$$2C_3H_6O_3 ==> C_5H_8O_4 + CO_2 \tag{9}$$

2-acetolactate conversion into 2,3-dihydroxyvalerate. In this reaction, a 2,3-dihydroxyvalerate molecule is obtained from a 2-acetolactate molecule, along with the formation of one NADP$^+$ molecule from one NADPH molecule. This reaction can be catalyzed by keto acid reductoisomerase enzymes (EC 1.1.1.86):

$$C_5H_8O_4 + NADPH + H^+ ==> C_5H_{10}O_4 + NADP^+ \tag{10}$$

2,3-dihydroxyvalerate conversions into ketoisovalerate. In this reaction, a ketoisovalerate molecule is obtained from a 2,3-dihydroxyvalerate molecule. This reaction can be catalyzed by dihydroxy acid dehydratase enzymes (EC 4.2.1.9):

$$C_5H_{10}O_4 ==> C_5H_8O_3 + H_2O \tag{11}$$

Ketoisovalerate conversion into isobutyraldehyde. In this reaction, an isobutyraldehyde molecule is obtained from a ketoisovalerate molecule. This reaction can be catalyzed by keto acid decarboxylase enzymes (EC 4.1.1.72):

$$C_5H_8O_3 ==> C_4H_8O + CO_2 \tag{12}$$

Isobutyraldehyde conversion into isobutanol. In this reaction, an isobutanol molecule is obtained from an isobutyraldehyde molecule along with the production of one NADP$^+$ molecule from one NADPH molecule. This reaction can be catalyzed by alcohol dehydrogenase enzymes (EC 1.1.1.2):

$$C_4H_8O + NADPH + H^+ ==> C_4H_{10}O + NADP^+ \tag{13}$$

From the above chemical equations, the overall stoichiometric of the multienzymatic system has theoretically no loss or gain of NADP$^+$ or NADPH. The overall reaction results in the use of two lactate molecules to produce one isobutanol molecule, obtaining 100% conversion efficiency, in accordance with the following reaction:

$$2C_3H_6O_3 ==> 2CO_2 + H_2O + C_4H_{10}O \tag{14}$$

c) Mixture of NAD(P)$^+$/NAD(P)H, by coupling enzymes which produce NAD(P)H with enzymes that produce NAD(P)$^+$, in accordance with the following reactions:

Lactate conversion into pyruvate. In this reaction, two NAD(P)H molecules are obtained from two NAD(P)$^+$ molecules along with the transformation of two lactate molecules into two pyruvate molecules. This reaction can be catalyzed by L-lactate dehydrogenase (EC 1.1.1.27) and/or D-lactate dehydrogenase enzymes (EC 1.1.1.28):

$$2C_3H_6O_3 + 2NAD(P)^+ ==> 2C_3H_4O_3 + 2NAD(P)H + 2H^+ \tag{15}$$

Pyruvate conversion into 2-acetolactate. In this reaction, one 2-acetolactate molecule is obtained from two pyruvate molecules. This reaction can be catalyzed by acetolactate synthase enzymes (EC 2.2.1.6):

$$2C_3H_4O_3 ==> C_5H_8O_4 + CO_2 \tag{16}$$

2-acetolactate conversion into 2,3-dihydroxyvalerate. In this reaction, one 2,3-dihydroxyvalerate molecule is formed from one 2-acetolactate molecule, along with the production of one NAD(P)$^+$ molecule from one NAD(P)H molecule. This reaction can be catalyzed by keto acid reductoisomerase enzymes (EC 1.1.1.86):

$$C_5H_8O_4 + NAD(P)H + H^+ ==> C_5H_{10}O_4 + NAD(P)^+ \tag{17}$$

2,3-dihydroxyvalerate conversion into ketoisovalerate. In this reaction, a ketoisovalerate molecule is obtained from a 2,3-dihydroxyvalerate molecule. This reaction can be catalyzed by dihydroxy acid dehydratase enzymes (EC 4.2.1.9):

$$C_5H_{10}O_4 ==> C_5H_8O_3 + H_2O \tag{18}$$

Ketoisovalerate conversion into isobutyraldehyde. In this reaction, one isobutyraldehyde molecule is obtained from one ketoisovalerate molecule. This reaction can be catalyzed by keto acid decarboxylase enzymes (EC 4.1.1.72):

$$C_5H_8O_3 ==> C_4H_8O + CO_2 \tag{19}$$

Isobutyraldehyde conversions into isobutanol. In this reaction, one isobutanol molecule is obtained from one isobutyraldehyde molecule, along with the production of one NAD(P)$^+$ molecule from one NAD(P)H molecule. This reaction may be catalyzed by alcohol dehydrogenase enzymes (EC 1.1.1.1 and EC 1.1.1.2):

$$C_4H_8O + NAD(P)H + H^+ ==> C_4H_{10}O + NAD(P)^+ \tag{20}$$

From the above chemical equations, the overall stoichiometric of the multienzymatic system has theoretically no loss or gain of NAD(P)$^+$ or NAD(P)H. The overall reaction results in the use of two lactate molecules to produce one isobutanol molecule, obtaining 100% conversion efficiency according to the following reaction:

$$2C_3H_6O_3 ==> 2CO_2 + H_2O + C_4H_{10}O \tag{21}$$

Figure 2:
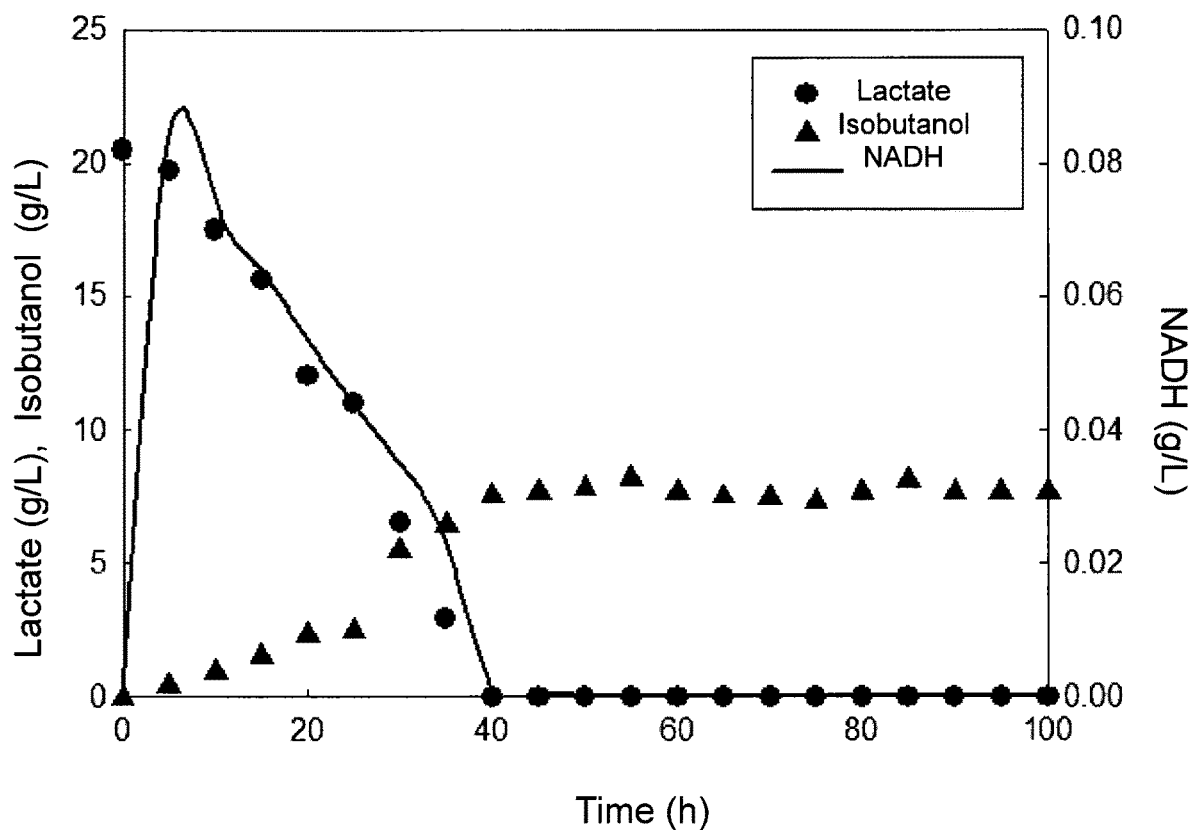
FIG. 2 shows a graph illustrating the behavior pattern of the batch production method of isobutanol.

A batch system was developed, to associate the NAD$^+$/NADH and/or NADP$^+$/NADPH regeneration system with isobutanol production from lactate, to use under different operating conditions (Table 26). The reaction mixture was formulated with the enzymes (Table 27), cofactors and coenzymes (at the concentrations described in the prior art), lactic acid and NAD$^+$ and/or NADP$^+$. In FIG. 2, the result of one of the conditions performed on the batch process is shown. In this particular condition, a volume of 1 L with an initial concentration of 20 g/L of L-lactate and 0.1 g/L of NAD$^+$ was used. The concentration of each of the enzymes (EC 1.1.1.27, EC 2.2.1.6, EC 1.1.1.86, EC 4.2.1.9, EC 4.1.1.72 and EC 1.1.1.1) in the reaction mixture was adjusted to 1 g/L. It should be highlighted that similar behaviors were obtained for the different conditions as shown in Tables 26 and 27.

In all cases, the reactions were initiated with the addition of lactate. From the beginning of the reaction, the reaction mixture was continuously sampled to determine the progress of the reaction. The NADH and/or NADPH concentration was measured over time on a Cary-60 spectrophotometer at a wavelength of 340 nm. The lactate and isobutanol were monitored by HPLC with refractive index detector using a Rezex ROA-Organic Acids H$^+$ column.

TABLE 26

Reaction conditions for isobutanol production from lactate in batch.

| Reaction Conditions | Value Range |
| --- | --- |
| Volumen de operación (L) | 1-100 |
| Temperature (° C.) | 20-37 |
| pH | 6-8 |
| Lactate (g/L) | 1-300 |
| $NAD^+$ and/or $NADP^+$ (g/L) | 0.01-10 |

TABLE 27

Enzyme used to formulate the enzyme mixture to produce isobutanol from lactate.

| Enzyme | Enzyme mixture Concentration (g/L) |
| --- | --- |
| Lactate dehydrogenase (EC 1.1.1.27 and/or EC 1.1.1.28) | 1-10 |
| Acetolactate sintase (EC 2.2.1.6) | 1-10 |
| Ketoacid reductoisomerase (EC 1.1.1.86) | 1-10 |
| Dihydroxy acid dehydratase (EC 4.2.1.9) | 1-10 |
| Ketoacid decarboxylase (EC 4.1.1.72) | 1-10 |
| Alcohol dehydrogenase (EC 1.1.1.1 and/or EC 1.1.1.2) | 1-10 |

In a system without NADH regeneration, the theoretical stoichiometric balance indicates that 147.8 g of NADH are required to convert 19.55 g of pyruvate (equivalent to 20 g of lactate) into 8.22 g of isobutanol. However, by coupling a $NAD^+$/NADH regenerating system, as suggested in the present invention, and in association with a lactate oxidation by the action of L-lactate dehydrogenase enzyme, only 0.1 g of $NAD^+$ to convert 20 g of lactate in 8.22 g of isobutanol is required.

Similar results to the ones described in the previous paragraphs, were obtained when the process was carried out with 0.1 g/L of $NADP^+$ and when a mixture of $NAD^+$ and $NADP^+$ was used at a concentration of 0.1 g/L.

The previously mentioned comments demonstrate that the isobutanol production from lactate in a batch process coupled with a $NAD^+$/NADH and/or $NADP^+$/NADPH regeneration system is possible.

Example 3. Enzymatic Isobutanol Production from Lactate, Coupled with the $NAD^+$/NADH and/or $NADP^+$/NADPH Regeneration System in a Continuous Process To demonstrate the possibility of coupling the enzymatic production of isobutanol from lactate, with a $NAD^+$/NADH and/or $NADP^+$/NADPH regeneration system, in a continuous process by using free enzymes, the following procedures were carried out:

Lactate was continuously converted into isobutanol in a reactor using free enzymes. The reaction mixture was formulated using the enzyme mixture (Table 27), cofactors and coenzymes (at the concentrations generally employed in the art), lactic acid, and $NAD^+$ and/or $NADP^+$. The operating conditions of the reactor are shown in Table 28. The inlet stream and outlet stream of the reactor were the same, in order to have a continuous process.

Figure 3:
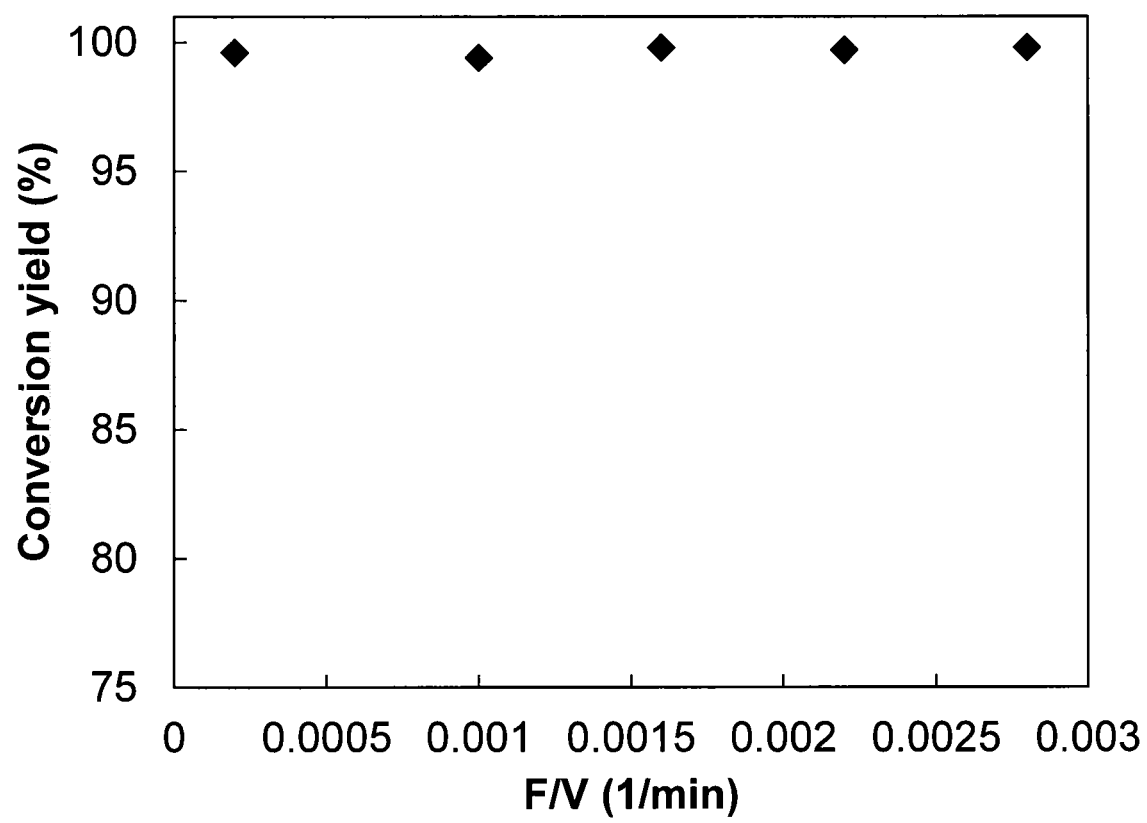
FIG. 3 shows a graph illustrating the behavior pattern of the method for continuous production of isobutanol in a CSTR reactor.

FIG. 3 shows some results obtained under several conditions performed in a CSTR, corresponding to an initial concentration of 20 g/L of D-lactate, and 0.1 g/L of $NADP^+$. The concentration of each of the enzymes (EC 1.1.1.28, EC 2.2.1.6, EC 1.1.1.86, EC 4.2.1.9, EC 4.1.1.72 and EC 1.1.1.2) in the reaction mixture were adjusted to 1 g/L. For all of these conditions, an operation volume of 50 L was used by varying flow conditions.

TABLE 28

Operating conditions in the reactor for isobutanol production from lactate.

| Variable | Intervalo |
| --- | --- |
| Operation Volume (L) | 1-100 |
| Lactate (g/L) | 1-300 |
| Temperature (° C.) | 20-37 |
| pH | 6-8 |
| $NAD^+$ and/or $NADP^+$ (g/L) | 0.01-10 |

The reaction was initiated in the same manner as in the batch process (see Example 2); subsequently, the addition and removal of the reaction medium took place in a continuous manner.

The output stream from the reactor was coupled to a reverse osmosis system, which separated the enzymes, cofactors, and coenzymes from isobutanol. The enzymes, cofactors, and coenzymes stream was recirculated into the reactor.

For all the conditions listed in Tables 27 and 28, the evolution of the reaction intermediates in the reactor outlet stream was monitored. The evolution of NADH and/or NADPH was measured on a Cary-60 spectrophotometer at a wavelength of 340 nm. The lactate and isobutanol were measured by HPLC with refractive index detector using a Rezex-ROA organic acids $H^+$ column.

As seen in FIG. 3, the conversion efficiency did not fluctuate in relation to the flow condition and it was close to 100%. In the same manner as in example 2. Such results demonstrate the possibility of coupling the enzymatic production of isobutanol from lactate, with a $NAD^+$/NADH and/or $NADP^+$/NADPH regenerating system, using only 0.1 g/L of $NADP^+$ to convert 20 g/L of lactate in a continuous process.

It should be highlighted that very similar conversion efficiencies were obtained for other conditions, as shown in Tables 27 and 28.

Example 4. Enzymatic Production of Isobutanol from Lactate, Coupled with the $NAD^+$/NADH and/or $NADP^+$/NADPH Regenerating System in a Continuous Process Using Immobilized Enzymes To demonstrate the possibility of coupling the enzymatic production of isobutanol from lactate, with a $NAD^+$/NADH and/or $NADP^+$/NADPH regeneration system, in a continuous process using immobilized enzymes, the following was carried out:

Isobutanol was continuously produced from lactate in a reactor in which each enzyme or enzyme mixture (Table 27) was immobilized in/on different carriers (Table 10), with varying quantities of immobilized protein. The operating conditions are shown in Table 29. The reaction mixture was formulated using the immobilized enzyme mixture (Table 27), cofactors and coenzymes (at the concentrations generally employed in the art), lactic acid, and $NAD^+$ and/or $NADP^+$.

TABLE 29

Operating conditions of the continuous reactor with immobilized
enzymes for the conversion of lactate into isobutanol.

| | |
|---|---|
| Reactor Volume (L) | 1-100 |
| Amount of immobilized enzyme (g/g). | $1 \times 10^{-3} - 1$ |
| Lactate (g/L) | 1-300 |
| Temperature (° C.) | 20-37 |
| pH | 6-8 |
| $NAD^+$ and/or $NADP^+$ (g/L) | 0.01-10 |

The output stream of the reactor was coupled to a reverse osmosis system, which recycles the mixture of cofactors, and coenzymes to the reactor and/or mixing tank. The initial concentration of $NAD^+$ and/or $NADP^+$ was 0.1 g/L, whereas the lactate concentration at the reactor inlet was varied according to Table 29. In all the conditions mentioned in tables 27 and 29, the evolution of the reaction intermediates was monitored along the tubular reactor. The change of NADH and/or NADPH was measured on a Cary-60 spectrophotometer at a wavelength of 340 nm. The lactate and isobutanol concentration were measured by HPLC with refractive index detector using a Rezex-ROA organic acids $H^+$ column.

Figure 4:
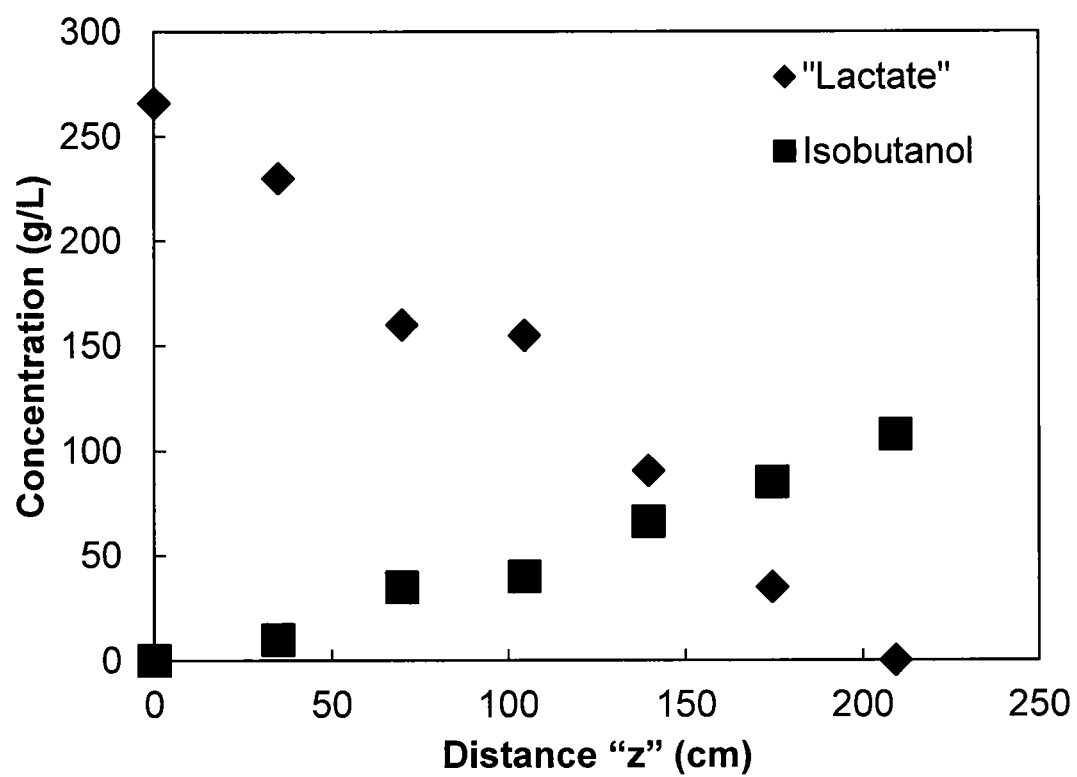
FIG. 4 shows a graph illustrating the behavior pattern of the method for continuous production of isobutanol along the z-axis of a PBR reactor.

FIG. 4 shows some results of performances under different conditions for the continuous process using immobilized enzymes packed in a tubular reactor. For all of those operating conditions, an operation volume of 50 L was used, with varying conditions of feed flow, with an input concentration of L-lactate of 264 g/L and 0.1 g/L of $NAD^+$. The amounts of each of the enzymes (EC 1.1.1.27, EC 2.2.1.6, EC 1.1.1.86, EC 4.2.1.9, EC 4.1.1.72 and EC 1.1.1.1) were adjusted to 0.01 gram per gram of carrier.

For this particular case, the reaction started when the mixture of cofactors, coenzymes, L-lactate, and $NAD^+$ entered the packed reactor.

As seen in FIG. 4, the L-lactate was converted into isobutanol, while the mixture was displaced through the packed tubular reactor to reach 100% conversion efficiency. The same happened under the different operating conditions listed in Tables 27 and 29. In the same manner as in examples 2 and 3, it was demonstrated that it is possible to associate the enzymatic production of isobutanol from lactate, with a $NAD^+$/NADH and/or $NADP^+$/NADPH regenerating system using only 0.1 g/L of $NAD^+$ to convert 264 g/L of lactate to 108 g/L of isobutanol.

In one aspect of the present invention, the total amount of $NAD^+$ and NADH used to convert two moles of lactate into one mole of isobutanol is less than 1 mol, less than 0.1 moles, or preferably less than 0.01 moles.

In one aspect of the present invention, the total amount of $NADP^+$ and NADPH used to convert two moles of lactate into one mole of isobutanol is less than one mole, less than 0.1 moles, or preferably less than 0.01 moles.

In one aspect of the present invention, the total amount of $NADP^+$/$NAD^+$ and NADPH/NADH used to convert two moles of lactate into one mole of isobutanol is less than one mole, less than 0.1 moles, or preferably less than 0.01 moles.

REFERENCES

The contents of the following references are hereby incorporated by reference in their entirety.

Atsumi S, Li Z, Liao J C. (2009). Acetolactate synthase from *Bacillus subtilis* serves as a 2-ketoisovalerate decarboxylase for isobutanol biosynthesis in *Escherichia coli*. Appl Environ Microbiol. 75(19):6306-6311.

Atsumi S, Wu T Y, Eckl E M, Hawkins S D, Buelter T, Liao J C. (2010) Engineering the isobutanol biosynthetic pathway in *Escherichia coli* by comparison of three aldehyde reductase/alcohol dehydrogenase genes. Appl Microbiol Biotechnol. 85(3):651-657.

Barak Z, Chipman D M, Gollop N. (1987). Physiological implications of the specificity of acetohydroxy acid synthase isozymes of enteric bacteria. J Bacteriol. 169(8): 3750-3756.

Bastian S, Liu X, Meyerowitz J T, Snow C D, Chen M M, Arnold F H. (2011). Engineered ketol-acid reductoisomerase and alcohol dehydrogenase enable anaerobic 2-methylpropan-1-ol production at theoretical yield in *Escherichia coli*. Metab Eng. 13(3):345-352.

Berezina O V, Zakharova N V, Yarotsky C V, Zverlov V V. (2012). Microbial producers of butanol. Appl. Biochem. Microbiol. 48(7):625-638.

Cetinel S, Caliskan H B, Yucesoy D T, Donatan A S, Yuca E, Urgen M, Karaguler N G, Tamerler C. (2013) Addressable self-immobilization of lactate dehydrogenase across multiple length scales. Biotechnol J. 8(2):262-272.

de la Plaza M, Fernandez de Palencia P, Peláez C, Requena T. Biochemical and molecular characterization of alpha-ketoisovalerate decarboxylase, an enzyme involved in the formation of aldehydes from amino acids by *Lactococcus lactis*. (2004). FEMS Microbiol Lett. 238(2):367-74.

Dickinson J R, Harrison S J, Hewlins M J. (1998) An investigation of the metabolism of valine to isobutyl alcohol in *Saccharomyces cerevisiae*. J. Biol. Chem. 273(40):25751-25756.

Flint D H, Emptage M H, Finnegan M G, Fu W, Johnson M K. (1993). The role and properties of the iron-sulfur cluster in *Escherichia coli* dihydroxy-acid dehydratase. J Biol Chem. 268(20):14732-14742.

Green Michael R., Sambrook Joseph. (2012). Molecular Cloning: A Laboratory Manual. Cold Spring Harbor Laboratory Press; 4th edition.

Holtzclaw W D, Chapman L F. (1975). Degradative acetolactate synthase of *Bacillus subtilis*: purification and properties. J Bacteriol. 121(3):917-922.

Jones D T, Woods D R. (1986). Acetone-butanol fermentation revisited. Microbiol. Rev. 50(4):484-524.

Kim S, Gu S A, Kim Y H, Kim K J. (2014) Crystal structure and thermodynamic properties of d-lactate dehydrogenase from *Lactobacillus jensenii*. Int J Biol Macromol. 68:151-7.

Li S, Wen J, Jia X. (2011) Engineering *Bacillus subtilis* for isobutanol production by heterologous Ehrlich pathway construction and the biosynthetic 2-ketoisovalerate precursor pathway overexpression. Appl Microbiol Biotechnol. 91(3):577-589.

Lia J, Tana S N, Ge H. (1996). Silica sol-gel immobilized amperometric biosensor for hydrogen peroxide Analytica Chimica Acta 335(1-2):137-145

Liu B, Hu R, Deng J. (1997). Characterization of immobilization of an enzyme in a modified Y zeolite matrix and its application to an amperometric glucose biosensor. Anal Chem. 69(13):2343-8.

Rane M J, Calvo K C. (1997). Reversal of the nucleotide specificity of ketol acid reductoisomerase by site-directed mutagenesis identifies the NADPH binding site. Arch Biochem Biophys. 338(1):83-89.

Torabi S F, Khajeh K, Ghasempur S, Ghaemi N, Siadat S O. (2007). Covalent attachment of cholesterol oxidase and horseradish peroxidase on perlite through silanization: activity, stability and co-immobilization. J Biotechnol. 131(2):111-20.

Wona K, Kima S, Kima K J, Park H W, Moona S J. (2005). Optimization of lipase entrapment in Ca-alginate gel beads. Process Biochem. 40:2149-2154.

What is claimed is:

1. A process of producing isobutanol, comprising:
   A) mixing water, lactate, an enzyme mixture, at least one cofactor, and at least one coenzyme, to prepare a reaction mixture;
   B) after A), initiating a catalytic reaction in the reaction mixture such that the lactate in the reaction mixture is catalytically converted to produce isobutanol; and
   C) separating the isobutanol from a reactant obtained by the catalytic reaction in B),
   wherein the enzyme mixture comprises at least one enzyme selected from the group consisting of lactate dehydrogenase (EC 1.1.1.27 and/or EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), alcohol dehydrogenase (EC 1.1.1.1 and/or EC 1.1.1.2), and analogues thereof, where the analogues of the at least one enzyme have the same enzymatic activity as the at least one enzyme, and
   the conversion of die lactate into isobutanol in B) is in association with a nicotinamide adenine dinucleotide ($NAD^+$)/reduced nicotinamide adenine dinucleotide (NADH) regenerating system, a nicotinamide adenine dinucleotide phosphate ($NADP^+$)/reduced nicotinamide adenine dinucleotide phosphate (NADPH) regenerating system, or both, and the process is not associated with growth of a microorganism, wherein, in B): the lactate in the reaction mixture is converted into pyruvate; pyruvate is converted into 2-acetolactate; 2-acetolactate is converted into 2,3-dihydroxyvalerate; 2,3-dihydroxyvalerate is converted into ketoisovalerate; ketoisovalerate is converted into isobutyraldehyde; and isobutyraldehyde is converted into isobutanol.

2. The process of claim 1, wherein an experimental yield of isobutanol from the lactate is from 98 to 100%.

3. The process of claim 1, wherein the enzyme mixture is prepared in a container prior to the mixing in A).

4. The process of claim 3, wherein the container is a pipe, a tank, or a reactor.

5. The process of claim 1, wherein, in A), the mixing is carried out in a container suitable to prepare the reaction mixture.

6. The process of claim 5, wherein the container is a pipe, a tank, a reactor, or a combination thereof.

7. The process of claim 1, wherein, in A), the mixing is carried out by a suitable method to promote interaction among the at least one enzyme and substrates.

8. The process of claim 1, wherein, in A), the mixing is carried out mechanically, pneumatically, or hydraulically, or a combination thereof.

9. The process of claim 1, wherein, in B), the catalytic reaction is carried out in a container or a reactor suitable to promote interactions among the enzymes and substrates.

10. The process of claim 9, wherein, in B), the catalytic reaction is carried out in a stirred tank reactor, a plug flow reactor, a fluidized bed reactor, a packed bed reactor, or a combination thereof.

11. The process of claim 1, wherein, in B), the catalytic reaction is carried out at a pH of from 2 to 12.

12. The process of claim 1, wherein, in C), the isobutanol is separated from the reactant by a suitable method to separate molecules based on their physicochemical properties.

13. The process of claim 1, wherein, in (C), the isobutanol is separated by membranes, distillation, evaporation, or a combination thereof.

14. The process of claim 13, wherein the membranes are reverse osmosis membranes, pervaporation membranes, nanofiltration membranes, or ultrafiltration membranes.

15. The process of claim 1, wherein the entire process is carried out continuously, semi-continuously, or in a batch manner.

16. The process of claim 1, wherein the lactate is at least one of L-lactate and D-lactate.

17. The process of claim 1, wherein a concentration of the lactate in the reaction mixture is at least 1 g/L.

18. The process of claim 1, wherein the at least one enzyme is immobilized, trapped, embedded, adhered, absorbed, attached, secured, or bound in/on a carrier.

19. The process of claim 18, wherein the carrier is at least one selected from the group consisting of zeolite, activated carbon, acrylamide, silica gel, agarose, alginate, and sand.

20. The process of claim 1, wherein a concentration of enzyme in the enzyme mixture is greater than 0.001 g/L.

21. The process of claim 18, wherein a concentration of enzyme in the enzyme mixture is greater than 0.001 g/g of the carrier.

22. The process of claim 1, wherein an amount of $NAD^+$/NADH and/or $NADP^+$/NADPH in the $NAD^+$/NADH and/or $NADP^+$/NADPH regeneration system is less than a stoichiometrically estimated amount.

23. The process of claim 1, wherein a total amount of $NAD^+$ and NADH used to convert two moles of the lactate into one mole of isobutanol is less than one mole.

24. The process of claim 1, wherein a total amount of $NADP^+$ and NADPH used to convert two moles of the lactate into one mole of isobutanol is less than one mole.

25. The process of claim 1, wherein a total amount of $NADP^+/NAD^+$ and NADPH/NADH used to convert two moles of the lactate into one mole of isobutanol is less than one mole.

26. The process of claim 1, wherein the separating in C) comprises:
   C-1) separating the reactant obtained by the catalytic reaction in B) into a first stream and a second stream, wherein the first stream comprises isobutanol and water, and the second stream comprises components in the reactant other than isobutanol and water; and
   C-2) separating the first stream into a first output stream and a second output stream, wherein the first output stream comprises isobutanol and the second output stream comprises water.

27. The process of claim 26, wherein the second stream is recirculated or reused by mixing into the reaction mixture in A), B), or both.

28. The process of claim 26, wherein, in C-1), the separation is carried out by a suitable method to separate molecules based on their physicochemical properties.

29. The process of claim 28, wherein the separation is carried out by membranes, distillation, evaporation, or a combination thereof.

30. The process of claim 26, wherein, in C-2), the separation is carried out by a suitable method to separate molecules based on their physicochemical properties.

31. The process of claim 30, wherein the separation is carried out by membranes, distillation, evaporation, or a combination thereof.

32. The process of claim 1, wherein the enzyme mixture comprises lactate dehydrogenase (EC 1.1.1.27 and/or EC 1.1.1.28), acetolactate synthase (EC 2.2.1.6), keto acid reductoisomerase (EC 1.1.1.86), dihydroxy acid dehydratase (EC 4.2.1.9), keto acid decarboxylase (EC 4.1.1.72), and alcohol dehydrogenase (EC 1.1.1.1 and/or EC 1.1.1.2).

33. The process of claim 1,
wherein, in A), the mixing is carried out in a first container suitable to prepare the reaction mixture, and
in B), the catalytic reaction is carried out in a second container or a reactor suitable to promote interactions among the enzymes and substrates.

* * * * *